US011408053B2

(12) United States Patent
Foley et al.

(10) Patent No.: US 11,408,053 B2
(45) Date of Patent: Aug. 9, 2022

(54) METHODS FOR SELECTIVE LEACHING AND EXTRACTION OF PRECIOUS METALS IN ORGANIC SOLVENTS

(71) Applicant: EXCIR WORKS CORP., Calgary (CA)

(72) Inventors: Stephen Foley, Saskatoon (CA); Hiwa Salimi, Saskatoon (CA); Loghman Moradi, Saskatoon (CA)

(73) Assignee: EXCIR WORKS CORP., Calgary (CA)

( * ) Notice: Subject to any disclaimer, the term of this patent is extended or adjusted under 35 U.S.C. 154(b) by 0 days.

(21) Appl. No.: 15/568,230

(22) PCT Filed: Apr. 21, 2016

(86) PCT No.: PCT/CA2016/050463
§ 371 (c)(1),
(2) Date: Oct. 20, 2017

(87) PCT Pub. No.: WO2016/168933
PCT Pub. Date: Oct. 27, 2016

(65) Prior Publication Data
US 2018/0112289 A1    Apr. 26, 2018

Related U.S. Application Data

(60) Provisional application No. 62/150,513, filed on Apr. 21, 2015, provisional application No. 62/152,066, filed on Apr. 24, 2015.

(51) Int. Cl.
| | |
|---|---|
| *C22B 11/00* | (2006.01) |
| *C22B 3/16* | (2006.01) |
| *C22B 3/06* | (2006.01) |
| *C22B 3/26* | (2006.01) |
| *C22B 3/28* | (2006.01) |
| *C22B 3/34* | (2006.01) |
| *C22B 3/36* | (2006.01) |
| *C22B 3/40* | (2006.01) |
| *C22B 3/44* | (2006.01) |
| *C07C 335/26* | (2006.01) |
| *C07D 207/06* | (2006.01) |
| *C07D 211/16* | (2006.01) |
| *C07D 295/215* | (2006.01) |
| *C22B 1/00* | (2006.01) |
| *C25C 1/20* | (2006.01) |
| *C25C 7/06* | (2006.01) |

(52) U.S. Cl.
CPC .......... *C22B 11/04* (2013.01); *C07C 335/26* (2013.01); *C07D 207/06* (2013.01); *C07D 211/16* (2013.01); *C07D 295/215* (2013.01); *C22B 1/00* (2013.01); *C22B 3/06* (2013.01); *C22B 3/16* (2013.01); *C22B 3/1608* (2013.01); *C22B 3/1616* (2013.01); *C22B 3/1625* (2013.01); *C22B 3/1666* (2013.01); *C22B 3/26* (2021.05); *C22B 3/28* (2021.05); *C22B 3/282* (2021.05); *C22B 3/284* (2021.05); *C22B 3/34* (2021.05); *C22B 3/36* (2021.05); *C22B 3/406* (2021.05); *C22B 3/44* (2013.01); *C25C 1/20* (2013.01); *C25C 7/06* (2013.01); *Y02P 10/20* (2015.11)

(58) Field of Classification Search
USPC .............................................. 423/22, 27–48
See application file for complete search history.

(56) References Cited

U.S. PATENT DOCUMENTS

| | | | | |
|---|---|---|---|---|
| 4,684,404 A | * | 8/1987 | Kalocsai | C22B 11/04 252/187.2 |
| 4,919,716 A | * | 4/1990 | Nakao | C22B 3/16 423/109 |
| 5,264,191 A | * | 11/1993 | Nakao | C07C 211/63 423/109 |
| 5,389,124 A | | 2/1995 | Nakao | |
| 5,607,619 A | | 3/1997 | Dadgar et al. | |
| 5,981,788 A | * | 11/1999 | Ofori et al. | |
| 6,319,389 B1 | | 11/2001 | Fountain et al. | |
| 2008/0261477 A1 | * | 10/2008 | Nomura | C22B 3/10 445/2 |
| 2011/0028306 A1 | * | 2/2011 | Variabel | C22B 3/065 502/5 |
| 2012/0228151 A1 | | 9/2012 | Loghman et al. | |

(Continued)

FOREIGN PATENT DOCUMENTS

| | | |
|---|---|---|
| CA | 2597937 A1 | 8/2006 |
| CA | 2666767 A1 | 4/2008 |

(Continued)

OTHER PUBLICATIONS

Dominguez et al, Liquid-liquid extraction of . . . benzoylthiourea complex Polyhedron 21, pp. 1429-1437. (Year: 2002).*
Vest et al., "Solvent extraction of gold with N-substituted benzoylthioureas". Fresenius' Journal of Analytical Chemistry, Sep. 1991 (Sep. 1991), vol. 341(9), pp. 566-568.
Oraby, E. A., et al., "The leaching of gold, silver and their alloys in alkaline glycine-peroxide 1, 2, 26 and 27 solutions and their adsorption on carbon". Hydrometallurgy, Dec. 31, 2014 (Dec. 31, 2014), vol. 152, pp. 199-203.
Nakao, Y., "Dissolution of noble metals in halogen-halide-polar organic solvent systems". Journal of the Chemical Society, Chemical Communications, 1992, vol. 5, pp. 426-427.

(Continued)

*Primary Examiner* — Steven J Bos
(74) *Attorney, Agent, or Firm* — Clark & Elbing LLP

(57) ABSTRACT

The present application relates to methods for leaching and extraction of precious metals. For example, the present application relates to methods of leaching gold, palladium and/or platinum from a substance comprising gold, palladium and/or platinum (such as a gold-containing ore or a platinum group metal (PGM) concentrate) using an organic solvent that is water-miscible or partially water-miscible.

30 Claims, 6 Drawing Sheets

(56) References Cited

U.S. PATENT DOCUMENTS

| | | | |
|---|---|---|---|
| 2013/0276284 A1* | 10/2013 | Brosseau | C22B 7/007 29/426.1 |
| 2016/0273060 A1 | 9/2016 | Bobadilla Fazzini et al. | |
| 2018/0142322 A1 | 5/2018 | Foley et al. | |

FOREIGN PATENT DOCUMENTS

| | | |
|---|---|---|
| CA | 2739662 A1 | 4/2010 |
| CA | 2738692 A1 | 7/2010 |
| CA | 2821042 A1 | 6/2012 |
| CA | 2884363 A1 | 3/2014 |
| CA | 2940830 A1 | 9/2015 |
| CA | 2949036 A1 | 11/2015 |
| CN | 1635168 A | 7/2005 |
| CN | 101220173 A | 7/2008 |
| CN | 101230421 A | 7/2008 |
| CN | 101535510 A | 9/2009 |
| CN | 102952947 A | 3/2013 |
| CN | 103320620 A | 9/2013 |
| CN | 103857811 A | 6/2014 |
| CN | 104060095 A | 9/2014 |
| CN | 104263938 A | 1/2015 |
| EP | 0124213 | 7/1984 |
| EP | 2226401 A1 | 9/2010 |
| EP | 2684622 A1 | 1/2014 |
| EP | 2765208 A1 | 8/2014 |
| GB | 1283389 * | 7/1972 |
| WO | 8200478 | 2/1982 |
| WO | 2006013568 A2 | 2/2006 |
| WO | 2006084273 A2 | 8/2006 |
| WO | 2006087313 A1 | 8/2006 |
| WO | 2006087413 A1 | 8/2006 |
| WO | 2006119611 A1 | 11/2006 |
| WO | 2007042604 A1 | 4/2007 |
| WO | 2007045034 A1 | 4/2007 |
| WO | 2007053947 A1 | 5/2007 |
| WO | 2007074360 A2 | 7/2007 |
| WO | 2007109841 A1 | 10/2007 |
| WO | 2007115399 A1 | 10/2007 |
| WO | 2008017731 A1 | 2/2008 |
| WO | 2008047010 A2 | 4/2008 |
| WO | 2008059770 A1 | 5/2008 |
| WO | 2008139412 A1 | 11/2008 |
| WO | 2008141443 A1 | 11/2008 |
| WO | 2009017434 A1 | 2/2009 |
| WO | 2009037596 A2 | 3/2009 |
| WO | 2009050334 A1 | 4/2009 |
| WO | 2009067039 A1 | 5/2009 |
| WO | 2009068735 A1 | 6/2009 |
| WO | 2009069005 A2 | 6/2009 |
| WO | 2009105832 A1 | 9/2009 |
| WO | 2009114045 A1 | 9/2009 |
| WO | 2009120373 A2 | 10/2009 |
| WO | 2009130345 A1 | 10/2009 |
| WO | 2009153409 A1 | 12/2009 |
| WO | 2010036144 A1 | 4/2010 |
| WO | 2010037169 A1 | 4/2010 |
| WO | 2010076030 A1 | 7/2010 |
| WO | 2010080050 A1 | 7/2010 |
| WO | 2010084364 A1 | 7/2010 |
| WO | 2010094161 A1 | 8/2010 |
| WO | 2010121329 A1 | 10/2010 |
| WO | 2011015991 A2 | 2/2011 |
| WO | 2011047070 A1 | 4/2011 |
| WO | 2011059380 A1 | 5/2011 |
| WO | 2011091231 A1 | 7/2011 |
| WO | 2011100821 A1 | 8/2011 |
| WO | 2011130622 A1 | 10/2011 |
| WO | 2011154603 A1 | 12/2011 |
| WO | 2011154607 A1 | 12/2011 |
| WO | 2011161597 A1 | 12/2011 |
| WO | 2012027532 A2 | 3/2012 |
| WO | 2012071342 A2 | 5/2012 |
| WO | 2012076981 A1 | 6/2012 |
| WO | 2012078019 A2 | 6/2012 |
| WO | 2012078020 A2 | 6/2012 |
| WO | 2012079129 A1 | 6/2012 |
| WO | 2012114165 A1 | 8/2012 |
| WO | 2012122774 A1 | 9/2012 |
| WO | 2012141607 A1 | 10/2012 |
| WO | 2012149631 A1 | 11/2012 |
| WO | 2012168915 A1 | 12/2012 |
| WO | 2012171480 A1 | 12/2012 |
| WO | 2012171481 A1 | 12/2012 |
| WO | 2012174349 A2 | 12/2012 |
| WO | 2013001365 A2 | 1/2013 |
| WO | 2013030450 A1 | 3/2013 |
| WO | 2013051715 A1 | 4/2013 |
| WO | 2013082614 A1 | 6/2013 |
| WO | 2013090517 A1 | 6/2013 |
| WO | 2013152424 A1 | 10/2013 |
| WO | 2014009928 A1 | 1/2014 |
| WO | 2014022946 A1 | 2/2014 |
| WO | 2014029017 A1 | 2/2014 |
| WO | 2014042131 A1 | 3/2014 |
| WO | 2014056034 A1 | 4/2014 |
| WO | 2014114746 A1 | 7/2014 |
| WO | 2014121150 A1 | 8/2014 |
| WO | 2014170863 A1 | 10/2014 |
| WO | 2014177765 A1 | 11/2014 |
| WO | 2014195586 A1 | 12/2014 |
| WO | 2015031943 A1 | 3/2015 |
| WO | 2015049421 A1 | 4/2015 |
| WO | 2015052658 A1 | 4/2015 |
| WO | 2015075502 A1 | 5/2015 |
| WO | 2015102865 A1 | 7/2015 |
| WO | 2015102867 A1 | 7/2015 |
| WO | 2015121799 A1 | 8/2015 |
| WO | 2015129385 A1 | 9/2015 |
| WO | 2015130607 | 9/2015 |
| WO | 2015147330 A1 | 10/2015 |
| WO | 2015172175 A1 | 11/2015 |
| WO | 2015178752 A1 | 11/2015 |
| WO | 2015181446 A1 | 12/2015 |
| WO | 2016008932 A1 | 1/2016 |
| WO | 2016168930 | 10/2017 |
| WO | 2016168933 | 10/2017 |

OTHER PUBLICATIONS

University of Saskatchewan, "Turning electronic waste into gold". Science 1, 26, 32, 37 and 39-44 Daily® web site, Jan. 28, 2016 (Jan. 28, 2016).

J. Cui, et al., "Metallurgical recovery of metals from electronic waste: A review". Journal of Hazardous Materials, 2008, vol. 158, pp. 228-256.

Written Opinion and International Search Report for PCT Application No. PCT/CA2016/050463 completed on Aug. 29, 2016.

Written Opinion and International Search Report for corresponding PCT Application No. PCT/CA2016/050459 completed on Aug. 26, 2016.

J. Avraamides et al., "Leaching of Silver with Copper (II) Ions in Aqueous Acetonitrile Solutions: Solubility of Salts and Equilibrium Constant Measurements in Sulphate Media". Elsevier Science Publishers B.V., Hydrometallurgy, 15 (1986), pp. 351-362.

Extended European Search Report for corresponding EP Patent Application No. 16782430.9 dated Dec. 14, 2018.

Office Action for corresponding Chinese Patent Application No. 201680036516.9 dated Dec. 29, 2018.

Akcil et al., "Precious Metal Recovery From Waste Printed Circuit Boards Using Cyanide and Non-Cyanide Lixiviants—A Review," Waste Management, 2015, vol. 45, pp. 258-271.

Alzate et al., "Recovery of Gold From Waste Electrical and Electronic Equipment (WEEE) Using Ammonium Persulfate," Waste Management, 2016, pp. 1-8.

Amey, "Gold," USGS Mineral Yearbook 2003 (Washington, D.C. USGS, 2003), pp. 34.1-34.9.

Anonymous, "Gold," Mining Journal, Jun. 11, 2004, pp. 19-24.

Aylmore et al., "Thiosulfate Leaching of Gold—A Review," Minerals Engineering, Feb. 2001, vol. 14(2), pp. 135-174.

(56) References Cited

OTHER PUBLICATIONS

Barbieri et al., "A New Environmentally Friendly Process for the Recovery of Gold From Electronic Waste," Environmental Chemistry Letters, 2010, vol. 8, pp. 171-178.
Berzowsky et al., "Recovery of Gold and Silver from Oxidation Leach Residues by Ammoniacal Thiosulfate Leaching," Presented at the 108th AIME Annual Meeting, New Orleans, Louisiana, Feb. 18-22, 1979, pp. 1-17.
Breuer et al., "The Reduction of Copper(Ii) and the Oxidation of Thiosulfate and Oxysulfur Anions in Gold Leaching Solutions," Hydrometallurgy, Jul. 2003, vol. 70(1-3), pp. 163-173.
Cayumil et al., "Concentration of Precious Metals During Their Recovery From Electronic Waste," Waste Management, 2015, pp. 1-10.
Chandra and Jeffrey., "A Fundamental Study of Ferric Oxalate for Dissolving Gold in Thiosulfate Solutions," Hydrometallurgy, Jun. 2005, vol. 77(3-4), pp. 191-201.
Chatterjee et al., "Efficient Management of E-Wastes," International Journal of Environmental Science and Technology, Jul. 2016.
Chehade et al., "Recovery of Gold, Silver, Palladium, and Copper from Waste Printed Circuit Boards," International Conference on Chemical, Civil and Environment Engineering, 2012, pp. 226-234.
Cheng et al., "Fast and Effective Gold Leaching from a Desulfurized Gold Ore Using Acidic Sodium Chlorate Solution at Low Temperature," Industrial & Engineering Chemistry Research, Nov. 2013, vol. 52, pp. 16622-16629.
Chmielewski et al., "Separation Technologies for Metals Recovery From Industrial Wastes," Hydrometallurgy, 1997, vol. 45, pp. 333-344.
Dai et al., "Modeling the Equilibrium Loading of Gold Onto Activated Carbon From Complex Cyanide Solutions," Mining, Metallurgy & Exploration, Nov. 2010, vol. 27(4), pp. 190-195.
Deschenes et al., "Effect of Oxygen and Lead Nitrate on the Cyanidation of a Sulphide Bearing Gold Ore," Minerals Engineering, Aug. 1995, vol. 8(8), pp. 923-931.
Doidge et al., "A Simple Primary Amide for the Selective Recovery of Gold from Secondary Resources," Angewandte Chemie International Edition, 2016, vol. 55, pp. 12436-12439.
Feng et al., "Ammoniacal Thiosulphate Leaching of Gold in the Presence of Pyrite," Hydrometallurgy, Aug. 2006, vol. 82(3-4), pp. 126-132.
Filmer et al., "A Comparison of Cyanide, Thiourea, and Chlorine as Lixiviants for Gold. Gold Mining, Metallurgy and Geology," Australasian Institute of Mining and Metallurgy, Melbourne, 1984, pp. 279-287.
Finkelstein et al., "An Aqueous Chlorination Process for the Treatment of Merrill Slimes and Gravity Concentrates From Gold Ores," Journal of the South African Institute of Mining and Metallurgy, Dec. 1966, vol. 67, pp. 196-215.
Geoffroy et al., "A Method for Leaching or Dissolving Gold From Ores or Precious Metal Scrap," The Journal of the Minerals, Aug. 2005, vol. 57(8), pp. 47-50.
Ghasem et al., "The Extraction of Gold from E-waste by Hydrometallurgy," Oriental Journal of Chemistry, 2015, vol. 31(1), pp. 113-120.
Gill et al., "New Leaching Agents for Oxides. The Reaction of Metal Oxides With the Mixed Non-Aqeous Systems Dimethyl Sulphoxide-sulphur Dioxide, Dimethyl Formamide-Sulphur Dioxide and Acetonitrile-Sulphur Dioxide," Hydrometallurgy, Dec. 1984, vol. 13(2), pp. 221-226.
Gonen., "Leaching of Finely Disseminated Gold Ore With Cyanide and Thiourea Solutions," Hydrometallurgy, Apr. 2003, vol. 69(1-3), pp. 169-176.
Groenewald., "The Dissolution of Gold in Acidic Solutions of Thiourea," Hydrometallurgy, Feb. 1976, vol. 1(3), pp. 277-290.
Grosse et al., "Leaching and Recovery of Gold Using Ammoniacal Thiosulfate Leach Liquors (a Review)," Hydrometallurgy, Apr. 2003, vol. 69(1-3), pp. 1-21.
Grosvenor et al., "New Interpretations of XPS Spectra of Nickel Metal and Oxides," Surface Science, 2006, vol. 600, pp. 1771-1779.
Gurung et al., "Recovery of Gold and Silver From Spent Mobile Phones by Means of Acidothiourea Leaching Followed by Adsorption Using Biosorbent Prepared From Persimmon Tannin," Hydrometallurgy, 2013, vol. 133, pp. 84-93.
Habashi et al., "A Textbook of Hydrometallurgy," Metallurgie Extractive Quebec: 2 edition, Jul. 1999.
Hageluken., "Improving Metal Returns and Eco-Efficiency in Electronics Recycling," IEEE, 2006, pp. 218-223.
Hageluken., "Improving Resource Recovery From Electronic Scrap Recycling—A Holistic Approach," Umicore Precious Metals Refining.
Hageluken., "Recycling of Electronic Scrap at Umicore's Integrated Metals Smelter and Refinery," World of Metallurgy—Erzmetall, May 2006, vol. 59(3), pp. 152-161.
Hasab et al., "Chloride-Hypochlorite Leaching of Gold From a Mechanically Activated Refractory Sulfide Concentrate," Hydrometallurgy, Jun. 2013, vol. 138, pp. 59-64.
Hasab et al., "Simultaneous Sulfide Oxidation and Gold Leaching of a Refractory Gold Concentrate by Chloride-Hypochlorite Solution," Minerals Engineering, 2013, vol. 50-51, pp. 140-142.
He and Xu., "Recycling Gold and Copper From Waste Printed Circuit Boards Using Chlorination Process," The Royal Society of Chemistry, 2015, vol. 5, pp. 8957-8964.
Hewitt et al., "The Ups and Downs of Gold Recycling Understanding Market Drivers and Industry Challenges," Boston Consulting Group, Mar. 2015, pp. 1-17.
Ikiz et al., "Dissolution Kinetics of Primary Chalcopyrite Ore in Hypochlorite Solution," Minerals Engineering, Jul. 2006, vol. 19(9), pp. 972-974.
Imrelucaci et al., "Technical and Environmental Assessment of Gold Recovery From Secondary Streams Obtained in the Processing of Waste Printed Circuit Boards," Chemical Engineering Journal, 2016, pp. 1-22.
Jadhav and Hocheng., "Hydrometallurgical Recovery of Metals from Large Printed Circuit Board Pieces," Scientific Reports, 2015, pp. 1-9.
Jeffrey et al., "A Kinetic Study That Compares the Leaching of Gold in the Cyanide, Thiosulfate, and Chloride Systems," Metallurgical and Materials Transactions B 32, Dec. 2001, vol. 32(6), pp. 979-986.
Jeffrey et al., "The Importance of Controlling Oxygen Addition During the Thiosulfate Leaching of Gold Ores," International Journal of Mineral Processing, Sep. 29, 2003, vol. 72(1-4), pp. 323-330.
Jiang et al., "Environmentally Benign Solution for Recycling Electronic Waste Using the Principles of Green Chemistry," Advanced Materials Research, 2014, vol. 878, pp. 406-412.
Jiang et al., "Improving the End-of-Life for Electronic Materials via Sustainable Recycling Methods," Procedia Environmental Sciences, 2012, vol. 16, pp. 485-490.
Jiang et al., Inorganic Chemistry, 2001, vol. 17 (3), pp. 343-348.
Jing Ying et al., "Thiourea Leaching Gold and Silver From the Printed Circuit Boards of Waste Mobile Phones," Waste Management, 2012, vol. 32, pp. 1209-1212.
Jujun et al., "A New Strain for Recovering Precious Metals From Waste Printed Circuit Boards," Waste Management, 2014, vol. 34, pp. 901-907.
Karamanoglu et al., "An Economic Analysis of the Recovery of Gold From CPU, Boards, and Connectors Using Aqua Regia," Desalination and Water Treatment, 2016, vol. 57, pp. 2570-2575.
Kaya., "Recovery of Metals and Nonmetals From Electronic Waste by Physical and Chemical Recycling Processes," Waste Management, 2016, vol. 57, pp. 64-90.
Kazakov et al., "Redox Potential of the Gold(I) Thiourea Complex," Russian Journal of Inorganic Chemistry, 1964, vol. 9 (5), pp. 708-709.
Keller., "Assessment of Gold Recovery Processes in Bangalore, India and Evaluation of an Alternative Recycling Path for Printed Wiring Boards," Swiss Federal Institute of Technology Zurich, Oct. 2006, pp. 1-105.
Chinese Patent Application No. 201680036516.9, Office Action dated Aug. 30, 2019—English Translation Available.
Chinese Patent Application No. CN20168036516, Office Action dated Feb. 25, 2020 (English Translation Available).

(56) References Cited

OTHER PUBLICATIONS

European Patent Application No. 16782430.9, Communication pursuant to Article 94(3) EPC dated Apr. 30, 2020.
Japanese Patent Application No. JP20170555706, Office Action dated Feb. 14, 2020 (English Translation Available).
Tasker et al., "Metal Complexes For Hydrometallurgy and Extraction," Comprehensive, Coordination Chemistry, Jan. 1, 2003, pp. 759-808.
U.S. Appl. No. 15/568,245, Notice of Allowance dated Mar. 25, 2020.
U.S. Appl. No. 15/568,245, Non-Final Office Action dated Oct. 24, 2019.
Kim et al., "Selective Recovery of Gold From Waste Mobile Phone PCBs by Hydrometallurgical Process," Journal of Hazardous Materials, Journal of Hazardous Materials, 2011, vol. 198, pp. 206-215.
Kondos et al., "Process Optimization Studies in Gold Cyanidation," Hydrometallurgy, Oct. 1995, vol. 39(1-3), pp. 235-250.
Korzenski., "A Sustainable Approach to Dealing with Electronic Waste," Evolv the Cleantech Solution to Waste.
Krzewska and Podsiadly., "Silver-Silver Thiourea Electrode for Determination of Free Thiourea Concentration in HClO4 Medium," Journal of Inorganic and Nuclear Chemistry, 1980, vol. 42, pp. 83-86.
Kumar et al., "Leaching of Metals From Waste Printed Circuit Boards (WPCBs) Using Sulfuric and Nitric Acids," Environmental Engineering and Management Journal, Oct. 2014, vol. 13(10), pp. 2601-2607.
Kumari et al., "Clean Process for Recovery of Metals and Recycling of Acid From the Leach Liquor of PCBs," Journal of Cleaner Production, 2015, pp. 1-9.
Lee et al., "A Study on the Recycling of Scrap Integrated Circuits by Leaching," Waste Management & Research, Jul. 2010, vol. 29(7), pp. 677-685.
Lekka et al., "Gold Recovery From Waste Electrical and Electronic Equipment by Electrodeposition: A Feasibility Study," Hydrometallurgy, 2015, vol. 157, pp. 97-106.
Leung et al., "Confronting a Toxic Blowback From the Electronics Trade," American Association for the Advancement of Science, Aug. 28, 2009, vol. 325, pp. 1055.
Li et al., "A Review of Gold Leaching in Acid Thiourea Solutions," Mineral Processing and Extractive Metallurgy Review, Sep. 2006, vol. 27(3), pp. 177-214.
Li et al., "Thiocyanate Hydrometallurgy for the Recovery of Gold Part II: The Leaching Kinetics," Hydrometallurgy, Feb. 2012, vol. 113-114, pp. 10-18.
Lin et al., "Organic Aqua Regia-Powerful Liquids for Dissolving Noble Metals," Angewandte Chemie International Edition, Oct. 2010, vol. 49(43), pp. 7929-7932.
Liu and Yen., "Effects of Sulphide Minerals and Dissolved Oxygen on the Gold and Silver Dissolution in Cyanide Solution," Minerals Engineering, Jan.-Feb. 1995, vol. 8(1-2), pp. 111-123.
Lu and Xu., "Precious Metals Recovery From Waste Printed Circuit Boards: A Review for Current Status and Perspective," Resources, Conservation and Recycling, 2016, vol. 113, pp. 28-39.
Mardsen and House., "The Chemistry of Gold Extraction," Society for Mining, Metallurgy, and Exploration, Inc., 2006, West Sussex, England.
Mecucci et al., "Leaching and Electrochemical Recovery of Copper, Lead and Tin From Scrap Printed Circuit Boards," Journal of Chemical Technology and Biotechnology, 2002, vol. 77, pp. 449-457.
Mellor et al., "A Comprehensive Treatise on Inorganic and Theoretical Chemistry," Longmans, Green and Company, 1923, vol. 3, pp. 499.
Munoz et al., "Noncyanide Leaching of an Auriferous Pyrite Ore From Ecuador," Minerals and Metallurgical Processing, 2000, vol. 17, pp. 198-204.
Nakao et al., "Reversible Dissolution/Deposition of Gold in Iodine-Iodide-Acetonitrile Systems," Chemical Communication, 1996, vol. 8, pp. 897-898.

Nam et al., "Use of Chloride-Hypochlorite Leachants to Recover Gold From Tailing," International Journal of Mineral Processing, Mar. 28, 2008, vol. 86(1-4), pp. 131-140.
Namias., "The Future of Electronic Waste Recycling in the United States: Obstacles and Domestic Solutions," Earth Engineering Center, Jul. 2013, pp. 1-51.
Nesbitt et al., "Determination of the Mechanism of the Chlorination of Gold in Aqueous Solutions," Industrial & Engineering Chemistry Research, Aug. 1990, vol. 29(8), pp. 1696-1700.
Oguchi et al., "Fate of Metals Contained in Waste Electrical and Electronic Equipment in a Municipal Waste Treatment Process," Waste Management, 2012, vol. 32, pp. 96-103.
Orgul and Atalay., "Reaction Chemistry of Gold Leaching in Thiourea Solution fora Turkish Gold Ore," Hydrometallurgy, Dec. 2002, vol. 67(1-3), pp. 71-77.
Owens., "Extreme Prospects High Gold Prices Are Making It Worthwhile to Look for Gold in Some Unusual Places," Nature, Mar. 14, 2013, vol. 495, pp. S4-S6.
Park and Fray., "Recovery of High Purity Precious Metals From Printed Circuit Boards," Journal of Hazardous Materials, 2009, vol. 164, pp. 1152-1158.
Parker et al., "An Application of Acetonitrile Leaching and Disproportionation Refining Segregated Copper From Roasted Concentrates and Ores," Hydrometallurgy, Aug. 1981, vol. 7(3), pp. 213-233.
Plessers., "Economic and Environmental Assessment and Optimization of Recycling Scenarios for IT Equipment in Developing Countries," KU Leuven Faculty of Engineering Science, 2012-2013, pp. 1-103.
Preisler et al., "Oxidation-Reduction Potentials of Thiol-Dithio Systems Thiourea-Formamidine Disulfide," Journal of the American Chemical Society, Feb. 1947, vol. 69(2), pp. 322-325.
Quinet et al., "Recovery of Precious Metals From Electronic Scrap by Hydrometallurgical Processing Routes," Minerals and Metallurgical Processing, 2005, vol. 22 (1), pp. 17.
Rabai and Epstein., "Systematic Design of Chemical Oscillators 83 Equilibria and Kinetics of the Fast Interaction Between Copper(II) and Thiosulfate Ions in Aqueous Solution," Inorganic Chemistry, Jul. 1992, vol. 31(15), pp. 3239-3242.
Ritchie et al., "Are There Realistic Alternatives to Cyanide as a Lixivant For Gold at the Present Time," Cyanide Social, Industrial and Economic Aspects, TMS, Warrendale, 2001, pp. 427-440.
Saadatjoo et al., "Recovery of Gold From Computer Circuit Board Scraps: The Study of the Effect of Different Reductants," Journal of Applied Chemistry, 2013, vol. 8(27), pp. 55-60.
Sahin et al., "A Potential Alternative for Precious Metal Recovery from E-waste: Iodine Leaching," Separation Science and Technology, 2015, vol. 50, pp. 2587-2595.
Sceresini., "Gold-Copper Ores," Elsevier Developments in Mineral Processing, 2005, vol. 15, pp. 789-824.
Schulze., "New Aspects in Thiourea Leaching of Precious Metals," Journal of Metals, Jun. 1984, vol. 36(6), pp. 62-65.
Senanayake., "Gold Leaching in Non-Cyanide Lixiviant Systems: Critical Issues on Fundamentals and Applications," Minerals Engineering, Jun. 2004, vol. 179(6), pp. 785-801.
Sheng et al., "Recovery of Gold From Computer Circuit Board Scrap Using Aqua Regia," Waste Management & Research, 2007, vol. 25, pp. 380-383.
U.S. Appl. No. 15/568,245, Notice of Allowance dated Aug. 11, 2020.
Veit et al., "Recovery of Copper From Printed Circuit Boards Scraps by Mechanical Processing and Electrometallurgy," Journal of Hazardous Materials, 2006, vol. B137, pp. 1704-1709.
Yoshimura et al., "Novel Process for Recycling Gold From Secondary Sources: Leaching of Gold by Dimethyl Sulfoxide Solutions Containing Copper Bromide and Precipitation With Water," Hydrometallurgy, Oct. 2014, vol. 149, pp. 177-182.
Zhang and Xu., "A Review of Current Progress of Recycling Technologies for Metals From Waste Electrical and Electronic Equipment," Journal of Cleaner Production, 2016, vol. 127, pp. 19-36.

(56) References Cited

OTHER PUBLICATIONS

Zhang et al., "A Study of the Gold Colloid Dissolution Kinetics in Oxygenated Ammoniacal Thiosulfate Solutions," Hydrometallurgy, 2004, vol. 74, pp. 243-257.

Zhang et al., "An Electrochemical Study of the Dissolution of Gold in Thiosulfate Solutions Part I: Alkaline Solutions," Journal of Applied Electrochemistry, 2003, vol. 33, pp. 767-775.

Aberasturi et al., "Recovery by Hydrometallurgical Extraction of the Platinum-Group Metals From Car Catalytic Converters," Minerals Engineering, 2011, vol. 24, pp. 505-513.

Chinese Patent Application No. CN201680036516, Office Action dated Sep. 28, 2020—English Translation Available.

Cooper and Beecham., "A Study of Platinum Group Metals in Three-Way Autocatalysts," Platinum Metals Review, 2013, vol. 57,(4), pp. 281-288.

Cui and Forssberg., "Mechanical Recycling of Waste Electric and Electronic Equipment: A Review", Journal of Hazardous Materials, 2003, vol. 99(3), pp. 243-263.

Dalrymple et al., "An Integrated Approach to Electronic Waste (WEEE) Recycling", Circuit World, 2007, vol. 33(2), pp. 52-58.

Deveci et al., "Extraction of Copper from Scrap TV Boards by Sulphuric Acid Leaching Under Oxidising Conditions," Conference Paper Jan. 2010, 8 pages.

Environment, The Conference Board Of Canada, Apr. 2016, 17 pages. Retrieved from the Internet: https://www.conferenceboard.ca/hcp/provincial/environment.aspx?AspxAutoDetectCookieSupport=1.

Foley., "Sustainable Technique Recovers Gold From E-waste Cheaply," University of Saskatchewan, Feb. 3, 2016. [Retrieved Feb. 3, 2020]. Retrieved from the Internet: https://phys.org/news/2016-02-sustainable-technique-recovers-gold-e-waste.html.

Fornalczyk and Saternus., "Removal of Platinum Group Metals From the Used Auto Catalytic Converter," Matelurgija, 2009, vol. 48(2), pp. 133-136.

Habashi et al., Principles of Extractive Metallurgy, New York: Gordon and Breach , 1980, vol. 1, 2nd edition, pp. 39.

Habashi et al., Principles of Extractive Metallurgy, New York: Gordon and Breach , 1980, vol. 2, 2nd edition, pp. 39.

Habashi et al., Principles of Extractive Metallurgy, New York: Gordon and Breach , 1980, vol. 3, 2nd edition, pp. 39.

Hagelüken., "Closing the Loop—Recycling of Automotive Catalysts," Metall, Jan. 2011, vol. 61(1-2), pp. 24-39.

Hagelüken., "Recycling the Platinum Group Metals: A European Perspective," Platinum Metals Review, 2012, vol. 56(1), 29.

Japanese Patent Application No. JP20170555706, Decision to Grant dated Feb. 16, 2021—English Translation not Available.

Japanese Patent Application No. JP20170555706, Office Action dated Sep. 14, 2020 (English Translation Available).

Khaliq et al., "Metal Extraction Processes for Electronic Waste and Existing Industrial Routes: A Review and Australian Perspective," Resources 2014, vol. 3, pp. 152-179.

Petter et al., "Evaluation of Gold and Silver Leaching From Printed Circuit Board of Cellphones," Waste Management, 2014, vol. 34, pp. 475-482.

Recycling Rates of Metals : A Status Report, International Resource Panel, May 2011, 48 pages.

Sharizan, I., "Gold leaching process and recovery from goldscraps using ascorbic acid", Universiti Malaysia Perlis, School of Materials Engineering, 2010, Perlis Malaysia, Retrieved from the Internet:. "title=" Link: http://dspace.unimap.edu.my/xmlui/bitstream/123456789/12930/1/p.+1-24.pdf>.>http://dspace.unimap.edu.my/xmlui/bitstream/123456789/12930/1/p.+1-24.pdf.

Shuey and Taylor., "Review of Pyrometallurgical Treatment of Electronic Scrap," Mining Engineering, Apr. 2005, vol. 57(4), pp. 67-70.

"The Social and Economic Impacts of Gold Mining", World Gold Council, Mar. 2015, 40 pages.

U.S. Appl. No. 15/568,245, Notice of Allowance dated Jan. 6, 2021.

Yoo and Lee., "Leaching of Copper and Silver From Ground Mobile Phone Printed Circuit Boards Using Nitric Acid," Journal of the Korean Institute of Resources Recycling , Jan. 2008, vol. 17(3), pp. 48-55.

Antrekowitsch et al., "Metallurgical Recycling of Electronic Scrap," TMS Annual Meet. 899-908 (2006).

"Basel Convention on the Control of Transboundary Movements of Hazardous Wastes and their Disposal," Basel, <https://treaties.un.org/Pages/ViewDetails.aspx?src=TREATY&mtdsg_no=XXVII-3&chapter=27&clang=_en>, dated Mar. 22, 1989 (13 pages).

"Canada: Light-Duty: Emissions," Transport Policy, <https://www.transportpolicy.net/standard/canada-light-duty-emissions/> retrieved Jan. 13, 2020 (11 pages).

"Cars and Light-Duty Trucks: Tier 3," DieselNet, <https://dieselnet.com/standards/US/ld_t3.php>, retrieved on Jan. 6, 2020 (9 pages).

Office Action for Chinese Patent Application No. 201680036516.9, dated Mar. 31, 2021 (4 pages).

"Columbus Metallurgical Complex," Sibanye Stillwater, <https://www.sibanyestillwater.com/business/americas/pgm-operations-americas/columbus-metallurgical-complex/>, retrieved on Jan. 13, 2020 (11 pages).

Condra, "Future Of E-Waste In The Circular Economy," human-I-T, <https://www.human-i-t.org/blogs/the-future-of-e-waste-in-the-circular-economy>, retrieved on May 15, 2020 (3 pages).

Crundwell et al., *Extractive Metallurgy of Nickel, Cobalt and Platinum-Group Metals*. ix-624 (2011).

"Cyanide Use in Gold Mining," Earthworks, <https://www.earthworks.org/issues/cyanide/>, retrieved Feb. 3, 2020 (3 pages).

"Electrical/Electronic Waste and Children's Health DRAFT," E-waste and Children's Health, <https://www.who.int/ceh/capacity/eWaste_and_childrens_health_DRAFT.pdf>, dated Jul. 21, 2015, retrieved on Feb. 11, 2020 (43 pages).

"Electronic Recyclers International® (ERI)," NERC, <https://nerc.org/advisory-members/member-spotlight/2015/03/electronic-recycling-international-(eri)>, retrieved on May 17, 2020 (9 pages).

"End of Life Vehicles," European Commission, <https://ec.europa.eu/environment/waste/elv/index.htm>, retrieved on Jan. 9, 2020 (2 pages).

"Waste from Electrical and Electronic Equipment (WEEE)," European Commission, <http://ec.europa.eu/environment/waste/weee/legis_en.htm>, dated Aug. 13, 2012, (5 pages).

"How much copper is there and where does it come from?," European Copper Institute: Copper Alliance, <https://copperalliance.eu/about-copper/copper-and-its-alloys/resources/>, retrieved on Sep. 23, 2020 (3 pages).

"Gold Properties," BullionVault, <https://www.bullionvault.com/gold-guide/gold-properties>, retrieved on Feb. 11, 2020 (4 pages).

"Gold Supply," World Gold Council, <https://www.gold.org/about-gold/gold-supply>, retrieved on Feb. 11, 2020 (2 pages).

Johnson Matthey, <https://matthey.com/en>, retrieved on Jan. 13, 2020 (1 page).

"U.S. Plug-in Electric Vehicle Sales by Model," Alternative Fuel Data Center, <https://afdc.energy.gov/data/10567>, dated Jan. 2020, retrieved on Jan. 13, 2020 (1 page).

Maverick, "China Creates $16-Billion Silk Road Gold Fund," Wall Street Daily, <https://www.wallstreetdaily.com/2015/06/14/china-silk-road-gold-fund/>, dated Jun. 14, 2015 (1 page).

"Mining in Canada," The Canadian Minerals and Metals Plan, <https://www.minescanada.ca/en/content/mining-canada-0>, retrieved on Jan. 6, 2020 (12 pages).

"Monitour: E-Trash Transparency Project," MIT, <http://senseable.mit.edu/monitour-app>, dated May 9, 2016, retrieved on Jan. 6, 2020 (1 page).

"Copper Facts," Government of Canada, <https://www.nrcan.gc.ca/our-natural-resources/minerals-mining/minerals-metals-facts/copper-facts/20506>, retrieved on Sep. 23, 2020 (8 pages).

"Chapter 3: Production and Uses of Platinum Group Metals," IPA, <https://ipa-news.de/assets/sustainability/IPA_Guidance/Chapter3_PGM_Guide.pdf>, retrieved on Jan. 6, 2020 (10 pages).

"Copper—Element information, properties and uses," Royal Society of Chemistry, <https://www.rsc.org/periodic-table/element/29/copper>, retrieved on Sep. 23, 2020 (4 pages).

(56) References Cited

OTHER PUBLICATIONS

Schulzke, "John Shegerian—CEO of Electronic Recyclers International," ideamensch, <https://ideamensch.com/john-shegerian/>, dated Dec. 20, 2012 (10 pages).
Screen captures from video titled: "Technology With a Heart of Recycled Gold," Dell, <https://www.dell.com/learn/US/en/uscorp1/videos~en/documents~gold-bayou.aspx?c=us&l=en&s=corp&cs=uscorp1>, retrieved on Feb. 3, 2020 (2 pages).
"Total Vehicle Sales," FRED Economic Data, <https://fred.stlouisfed.org/series/TOTALSA#0.2020>, retrieved on Jan. 14, 2020 (1 page).
Crundwell et al., *Extractive Metallurgy of Nickel, Cobalt and Platinum-Group Metals*, ix-610 (2011).
Non-Final Office Action for U.S. Appl. No. 15/568,230, dated Apr. 6, 2021 (27 pages).
"Utilisation and Fields of Application of Gold," Gold.info, <https://www.gold.info/en/application-of-gold/>, retrieved on Feb. 11, 2020 (3 pages).
"What Is An End Of Life Vehicle", Green Vehicle, <https://greenvehicledisposal.com/what-is-an-end-of-life-vehicle/#:~:text=In%20the%20United%20States%2010,vehicles%20yearly%20in%20Ontario%20alone>, retrieved on Jan. 9, 2020 (4 pages).
Tulumba, "Overall US Auto Industry Sales Figures", Good Car Bad Car. Retrieved on Jan. 13, 2020 from <https://www.goodcarbadcar.net/USA-auto-industry-total-sales-figures/> (1 page).
Plaksin, I.N., and Kozhukhova, M.A., 1941, "The Solubility of Gold and Silver in Thiourea," Compt. Rend. Acad. Sci., USSR, vol. 31, pp. 671-674, (CA 35:561).
Office Action for Indian Patent Application No. 201717040510, dated Jan. Feb. 22, 2021 (7 pages).
Notice of Allowance for U.S. Appl. No. 15/568,245, dated Apr. 28, 2021 (25 pages).
Notice of Completing Formalities for Patent Registration for Chinese Patent Application No. 201680036516.9 dated Jul. 30, 2021 (4 pages).
Amey, "Gold," USGS Mineral Yearbook 2003. 32.1-32.13.
Banhegyi, "What Is the Difference Between Compatibilizer and Coupling Agents for Polymer Composites?" Research Gate, 2014.
Birak et al., "Dense Nonaqueous Phase Liquids at Former Manufactured Gas Plants: Challenges to Modeling and Remediation," J Contam Hydrol. 105(3-4): 81-98 (2009).
"European Union Risk Assessment Report: 2,2',6,6'-Tetrabromo-4,4'-Isopropylidenediphenol (Tetrabromobisphenol-A or TBBP-A) Part II—Human Health," *European Chemicals Bureau vol. 63* (2006).
Friedrich, "Chapter 1: Routes for Achieving Multifunctionality in Reinforced Polymers and Composite Structures," *Multifunctionality of Polymer Composites*. 3-41 (2015).
Gdoutos, "Fracture Mechanics: An Introduction, 2nd edition," *Solid Mechanics and Its Applications*. G.M.L. Gladwell, 2005.
George, "Gold," USGS Minerals Yearbook 2004. 32.1-32.13.
Herat et al., "Environmental Impacts and Use of Brominated Flame Retardants in Electrical and Electronic Equipment," The Environmentalist. 28: 348-357 (2008).
Notice of Allowance for U.S. Appl. No. 15/568,245, dated Aug. 25, 2021.
Zhang et al., "Removal of Brominated Flame Retardant From Electrical and Electronic Waste Plastic by Solvothermal Technique," J Hazard Mater. 221-222: 193-198 (2012).
Office Action for Canadian Patent Application No. 2983350, dated Mar. 2, 2022 (4 pages).
Office Action for Canadian Patent Application No. 2983353, dated Mar. 3, 2022 (5 pages).
Guo et al., "Performance and Thermal Behavior of Wood Plastic Composite Produced by Nonmetals of Pulverized Waste Printed Circuit Boards," Journal of Hazardous Materials. 179(1-3):203-207 (2010).
International Preliminary Report on Patentability for International Patent Application No. PCT/CA2016/050459, dated Oct. 24, 2017 (7 pages).
International Preliminary Report on Patentability for International Patent Application No. PCT/CA2016/050463, dated Oct. 24, 2017 (8 pages).
International Search Report and Written Opinion for International Patent Application No. PCT/CA2021/051102, dated Nov. 22, 2021 (13 pages).
International Search Report and Written Opinion for International Patent Application No. PCT/CA2021/051351, dated Dec. 20, 2021 (13 pages).
International Search Report and Written Opinion for International Patent Application No. PCT/CA2021/051385, dated Dec. 15, 2021 (15 pages).
Office Action for Japanese Patent Application No. 2021-070523, dated Feb. 3, 2022 (2 pages).
Oraby et al., "The Selective Leaching of Copper From a Gold-copper Concentrate in Glycine Solutions," Hydrometallurgy. 150:14-19 (2014).
Notice of Allowance for U.S. Appl. No. 15/568,245, dated Dec. 16, 2021 (7 pages).
Corrected Notice of Allowability for U.S. Appl. No. 15/568,245, dated Feb. 16, 2022 (2 pages).
Communication Pursuant to Article 94(3) EPC for European Patent Application No. 16782430.9, dated Mar. 31, 2022 (5 pages).
Notice of Allowance for U.S. Appl. No. 15/568,245, dated Mar. 30, 2022 (5 pages).

\* cited by examiner

METHODS FOR SELECTIVE LEACHING AND EXTRACTION OF PRECIOUS METALS IN ORGANIC SOLVENTS

CROSS-REFERENCE TO RELATED APPLICATIONS

The present application is a National Stage of International Application No. PCT/CA2016/050463 filed Apr. 21, 2016 which claims the benefit of priority from U.S. Provisional Patent Application No. 62/150,513 (Filed: Apr. 21, 2015) and U.S. Provisional Patent Application No. 62/152,066 (Filed: Apr. 24, 2015), the contents of each of which are incorporated herein by reference.

FIELD

The present application relates to methods for leaching and extraction of precious metals. For example, the present application relates to methods of leaching gold, palladium and/or platinum from a substance comprising such precious metals (such as a gold-containing ore or a platinum group metal (PGM) concentrate) using an organic solvent that is water-miscible or partially water-miscible.

BACKGROUND

Gold is an element in the periodic table which belongs to the same group as silver and copper. It is usually found in combination with these metals in ores. The average concentration of copper and silver in Earth's crust is 50 and 0.07 ppm (parts per million) respectively while for gold it is just 0.005 ppm.

Ore deposits with a concentration of 0.5 ppm or higher are considered to be economically recoverable. Due to its limited sources, gold recovery not only from ores, but also from secondary sources has become more and more important during the last decades. The annual production of gold from the gold mining industry is more than 2500 tonnes worldwide[2]. In addition, about 900 tonnes of secondary gold is recovered from different sources such as but not limited to anode slime and jewelry, dentistry and electronic scraps[3].

The most commonly used process for gold recovery from ore includes the use of highly toxic inorganic cyanides (e.g., NaCN, KCN) to convert gold(0) into a water-soluble $Au(CN)_2^-$ coordination complex by a process known as leaching. An example of a known process 10 for gold recovery using cyanide leaching is shown in FIG. 1. In process 10, low grade ore 12 is crushed and ground 14 then leached 16 with a basic solution of NaCN for 16 to 48 hours depending on ore type. Because of some environmental accidents in various gold mines around the world, gold leaching by cyanidation has been prohibited in many countries[4]. Therefore, considerable efforts have been made to find an alternative to cyanide and a variety of leaching reagents have been studied and proposed[5,6].

Generally, following gold dissolution in the cyanide solution, gold is recovered by activated carbon adsorption (e.g. step 18 in process 10 of FIG. 1 wherein, for example 0.1 to 1 kg activated carbon per ton ore is used), or by the zinc cementation process. The activated carbon adsorption process is considerably more common[7,8]. For example, 4 to 8 kg gold can be adsorbed by 1 ton activated carbon in 4 to 8 steps over a time period of 4 to 8 hours.

As shown in FIG. 1, following the carbon adsorption step 18, the loaded activated carbon is washed 20 with low concentrated HCl to remove impurities such as adsorbed Zn, Ca, Fe, Cu and Ag then gold desorption (elution) 22 is done by using, for example 1% NaOH and 0.1 to 0.2% NaCN solution at a high temperature (e.g. 110° C.) for 36 to 72 hours. Pure gold 24 can be obtained, for example by electrowinning or reduction. The whole process time for gold recovery using a process like the process 10 shown in FIG. 1 is 46-110 hours.

Processes for gold recovery which use activated carbon may suffer from several drawbacks such as but not limited to low selectivity, very long procedures, loss of gold product, high temperature requirements, and further consumption of cyanide for desorption of gold from activated carbon, all of which may bring additional costs during the gold recovery process[9].

Although considerable effort has been undertaken to replace cyanide, none of the reported leaching reagents has been used in the industrialization of gold production due, for example to drawbacks such as (i) high reagent consumption, (ii) complex chemistry, (iii) lack of industrial techniques for the recovery of gold from their resulting solutions, and (iv) low rate of gold recovery compared to cyanide. Drawbacks such as toxicity, cost, long reaction times and poor selectivity are also associated with known systems. Thus, it may be desirable to develop more effective leachants with, for example, higher efficiency and/or lower toxicity from both an environmental and an economical viewpoint.

Cyanide Leaching

For more than a century, cyanidation has remained the dominant process for extraction and recovery of gold from ore. Metallic gold can be dissolved in an alkaline solution of potassium or sodium cyanide in the presence of dissolved molecular oxygen (reaction 1):

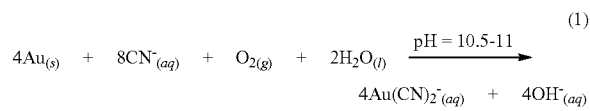

(1)

$$4Au_{(s)} + 8CN^-_{(aq)} + O_{2(g)} + 2H_2O_{(l)} \xrightarrow{pH=10.5-11} 4Au(CN)_2^-_{(aq)} + 4OH^-_{(aq)}$$

In neutral or acidic conditions, over 99% of the cyanide will exist as highly poisonous HCN gas. By increasing pH, it is converted to free cyanide ion so that at a pH of 9.3, $CN^-$ and HCN are in equilibrium, with 50% of each present. At a pH of 11, over 99% of the cyanide remains in solution as $CN^-$.[10] The free cyanide ion is a very strong ligand which can form a highly stable complex with gold, $Au(CN)_2^-$, in aqueous solution. With stoichiometric ratios, gold dissolution in alkaline cyanide solution is slow, but by increasing the cyanide concentration, the leaching rate will increase until a maximum is reached (0.075 w/w % KCN or 0.06% NaCN) and after that the rate of dissolution remains constant[11].

Before cyanide treatment, the gold ore is typically crushed and ground to decrease the size of the ore particles to 75 microns or less to provide a larger contact surface area between the gold and the leaching solution. Depending on the ore type, the cyanide consumption varies from about 0.25 to 2 kg of cyanide per tonne of ore and the rate of gold dissolution in cyanide takes 16 to 48 hours[11]. The cyanide consumption increases when the refractoriness of the gold ore is increased. A refractory gold ore is a gold-containing ore that is resistant to recovery by direct cyanidation. Other minerals and metals are also dissolved in the alkaline cyanide solution and they usually consume cyanide and oxygen and thus reduce the overall efficiency of gold leaching.

For example, copper minerals such as chalcocite (Cu₂S) and cuprite (Cu₂O) can form a variety of cyanide complexes such as CuCN, $Cu(CN)_2^-$, $Cu(CN)_3^{2-}$ and $Cu(CN)_4^{3-}$ and iron sulfides like pyrrhotite (Fe₇S₈), pyrite (FeS₂) and arsenopyrite (FeAsS) form highly stable $Fe(CN)_6^{4-}$ and $Fe(CN)_6^{3-}$ complexes[12]. In addition, most sulfide minerals have a detrimental effect on gold leaching since they may passivate the surface of gold and consume cyanide and oxygen. However, some other minerals such as galena (PbS) can improve gold leaching kinetics by preventing formation of a passivation layer on the gold surface[13].

Although cyanide is still the main leaching reagent for gold recovery in the mining industry, it suffers from several drawbacks such as but not limited to high toxicity, slow leaching kinetics and low gold extraction for refractory ores. Considerable efforts have thus been made to find an alternative to cyanide.

Gold Recovery from Cyanide Solution

There are several techniques for gold recovery from cyanide leach liquors like carbon adsorption, zinc cementation and solvent extraction with carbon adsorption being by far the more common technique[14,15]. In the carbon adsorption technique, after gold is leached into cyanide solution, activated carbon is applied for selective gold adsorption to separate $AuCN_2^-$ from other metals and impurities. 0.1 to 1 kg activated carbon per tonne of ore is usually applied in 4 to 8 steps for complete adsorption of $Au(CN)_2^-$ complex from cyanide solution which takes 4 to 8 hours. The loaded activated carbon is usually washed with a low concentration HCl solution to remove other impurities such as Fe, Cu, Zn, Ca, and Ag. The dicyanoaurate(I) complex is then removed from the activated carbon in an elution step by washing the loaded activated carbon with a fresh basic sodium cyanide solution at 110° C. for 36 to 72 hours[10,16]. The desorbed $Au(CN)_2^-$ complex is finally reduced to elemental gold by electrowinning or reduction.

The activated carbon method suffers from several drawbacks such as but not limited to low selectivity, very long procedures, loss of some gold product, and high temperature requirements[17].

Alternatives to Cyanide

Due to the high toxicity and environmental problems of cyanide, there has been a quest to find useful alternatives. In recent years, some alternatives to cyanide have been reported to leach gold ore efficiently. Some of the useful reported leaching reagents are thiosulfate, thiocyanite, thiourea, and chloride in combination with an oxidizing agent like HNO₃, H₂O₂ and hypochlorite.

Thiosulfate Leaching

Thiosulfate is the most studied alternative to cyanide. Gold can be leached in alkaline aqueous solutions (pH=9.5-10.5) of thiosulfate in the presence of oxidizing agents like O₂ and copper(II) ions. The rate of gold dissolution becomes slower in the absence of copper (II) ions[18]. Ammonia is usually used to accelerate the rate of gold leaching in this media. It has an efficient role to stabilize the intermediate oxidation products of gold, decreasing the rate of thiosulfate oxidation by $Cu^{2+}$, preventing the formation of insoluble components like sulfides on the gold surface and keeping a high concentration of $Cu^{2+}$ by forming $Cu(NH_3)_4^{2+}$ during the leaching process[19,20]. Oxygen has a dual role by oxidation of $Cu(NH_3)_2^+$ to $Cu(NH_3)_4^{2+}$ or direct oxidation of the gold surface. The overall balanced equation of gold dissolution in thiosulfate media is shown in the following reaction[21] (2):

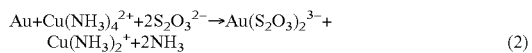

Compared to the cyanidation process, thiosulfate leaching has some advantages such as but not limited to fast leaching kinetics, lower toxicity and higher gold recovery in the case of some refractory gold ores[22,23]. However, it suffers from some major drawbacks such as but not limited to complex chemistry, toxicity of ammonia, ineffectiveness of activated carbon for desorption of leached gold, and high consumption of thiosulfate.

For example, the copper(II) itself consumes thiosulfate resulting in high consumption of both thiosulfate and copper and the resulting tetrathionate ($S_4O_6^{2-}$) decomposes to elemental sulfur and forms sulfides such as CuS which increases the gold passivation during the leaching process (reaction 3)[24,25].

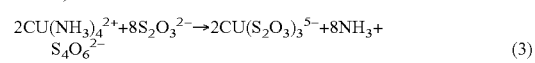

Thiourea

Thiourea is another well-studied leaching reagent which can dissolve gold in acidic media based on the following reaction (4)[26]:

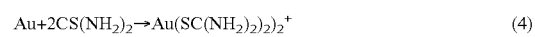

Different oxidizing reagents such as but not limited to hydrogen peroxide, sodium peroxide, oxygen, ozone and ferric ion can be used in combination with thiourea to dissolve gold. Among these oxidizing reagents, ferric ion in sulfuric acid solution is a useful one (reaction 5)[27].

However, thiourea is not stable in acidic media in the presence of ferric ion and is decomposed to sulfur and cyanamide[28]. Addition of a reducing agent such as SO₂ decreases the thiourea consumption by preventing its oxidation[29]. The kinetics of gold leaching in thiourea solution are much faster than the cyanidation process because of nongaseous oxidants such as but not limited to hydrogen peroxide and ferric sulfate which are used instead of oxygen which is used in the cyanidation process[30]. However, gold recovery and reagent consumption with cyanide is more economical than thiourea[31].

Complexation with base metals such as copper accelerates thiourea consumption and decreases gold leaching kinetics. Thermal degradation, oxidation by the ferric sulfate and air are the other reasons for high consumption of thiourea[32]. Thiourea's commercial application has been hindered due to its high consumption and no existence of applicable industrial techniques for the recovery of gold from its solution. Although thiourea has a lower toxicity compared to cyanide, it is suspected to be a carcinogen agent and is treated with caution[33].

Chloride Solution Containing an Oxidizing Agent

Concentrated hydrochloric acid in combination with powerful oxidizing agents is known as a strong leaching reagent for leaching precious metals, for example from scraps and secondary sources[34]. A hot solution of concentrated HCl mixed with concentrated HNO₃ (known as aqua regia) or hydrogen peroxide can dissolve gold according to the following chemical reactions (see reactions 6 and 7) resulting in the formation of a stable $AuC_{14}^-$ complex[35].

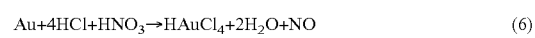

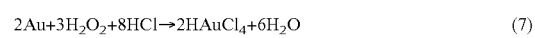

Apart from these oxidants, chlorine gas can also be used which forms the same gold species[36]. Chlorine had been used to dissolve gold from ores and concentrates during the second half of the 19th century until it was gradually replaced by the more economical alkaline cyanide leaching. In all cases, the dissolution rate is faster compared to cyanide, however, due to high concentration of HCl, all of these solutions are highly corrosive and toxic and in the case of gold ore treatment, their consumption is not economical[37].

Chloride/Hypochlorite

Chloride/hypochlorite solutions have been recognized as another alternative leaching reagent to cyanide which can dissolve gold in a wide range of pH values[38]. Depending on the solution's pH, three different oxidizing species can be formed in hypochlorite solutions. At pH>7.5, hypochlorite ion ($OCl^-$) is the dominant species while for pH values between 3.5 and 7.5, hypochlorous acid (HOCl) acts as oxidizing agent and for pH less than 3.5, nascent chlorine gas ($Cl_2$) is formed. Among these three species, HOCl is the most effective oxidizing agent to leach gold as the $[AuCl_4]^-$ (reaction 8)[39].

  (8)

In a solution containing 100 g/L NaCl, the $[AuCl_4]^-$ is stable in the pH range of 0-8 and potentials greater than 0.9 V[40]. The chloride-hypochlorite solution is a useful leaching reagent, for example for refractory gold ores. Because of low acidity, it does not produce a corrosion media; however the reagents consumption is still high[41,42]. The main drawback of this leaching reagent is that the percentage of leached gold is usually less than 85%[43].

Gold Leaching in Organic Solvents

Polar and water miscible organic solvents have been investigated for dissolution of some transition metals like silver and copper[44,45,46]. In some cases better leaching efficiency has been achieved in particular mixtures of water-solvent or pure solvent. There are also a few examples of gold leaching in organic solvents like DMSO, methanol, acetone, N,N-dimethylformamide and acetonitrile[45,47,48]. For example, Yukimichi investigated the dissolution rate of gold, silver and palladium in different halogen-halide-polar organic solvent systems and in the case of gold, he proved it could be dissolved in a mixture of a halide source, a halogen such as chlorine gas, bromine, iodine, and an organic solvent like methanol or MeCN. Among investigated systems, mixtures of chlorine gas, acetonitrile and $Me_3NHCl$ (as chloride source) dissolved gold most effectively; even faster than aqua regia[48].

SUMMARY

The present studies disclose the use of a polar, water-miscible or partially water-miscible organic solvent in combination with conventional leaching reagents. Conventional leaching reagents, for example, acidified chloride solutions containing an oxidizing agent have not been investigated for gold leaching directly in organic solvents. This new recovery system may, for example, simplify the recovery process, save considerable time and energy and due to the recoverability of the organic solvent, produce less waste.

Accordingly, the present application includes a method of leaching gold, palladium and/or platinum from a substance comprising gold, palladium and/or platinum, the method comprising contacting the substance with a mixture comprising:
 (a) an acid;
 (b) an oxidizing agent; and
 (c) a water-miscible or partially water-miscible organic solvent, under conditions to leach the gold, palladium and/or platinum from the substance.

In another embodiment of the present application, the conditions to leach the gold, palladium and/or platinum from the substance comprise stirring the substance and the mixture for a time of about 0.1 minute to about 30 minutes at a temperature of about 10° C. to about 80° C.

In an embodiment, the acid in the mixture is selected from HCl, $H_2SO_4$, HBr, $HNO_3$, $H_3PO_4$ and HI.

In another embodiment, the acid is an aqueous solution of HCl having a concentration of from about 0.01 M to about 2.5 M.

In an embodiment, the oxidizing agent in the mixture is selected from $H_2O_2$, $Cl_2$, $Br_2$, $I_2$, $Ca(ClO)_2$, $HNO_3$, $MnO_2$, $KMnO_4$ and $K_2Cr_2O_7$. In another embodiment, the oxidizing agent is $H_2O_2$ or $Ca(ClO)_2$.

In another embodiment of the present application, the water-miscible or partially water-miscible organic solvent in the mixture is selected from acetic acid, ethyl acetate and acetonitrile.

In an embodiment, the mixture further comprises a metal halide, an ammonium halide, a tetraalkylammonium halide or a combination thereof. In another embodiment, the mixture further comprises the metal halide and the metal halide is $CaCl_2$. In a further embodiment, the $CaCl_2$ in the mixture has a concentration of from about 0.05M to about 1.5M. It is an embodiment of the present application that reagent (a) in the mixture is HCl, reagent (b) in the mixture is $H_2O_2$ and reagent (c) in the mixture is acetic acid.

In an embodiment, the substance comprising gold, palladium and/or platinum is a gold-containing substance. In an embodiment, the gold-containing substance further comprises iron, copper, cobalt, or nickel or a combination thereof, and the method selectively dissolves the gold from the gold-containing substance. In another embodiment of the present application, the gold-containing substance is a gold-containing ore.

In an embodiment, the method provides a gold dissolution rate of at least 500 $gm^{-2}h^{-1}$, at least 1000 $gm^{-2}h^{-1}$ or at least 5000 $gm^{-2}h^{-1}$. In another embodiment, the method provides a gold dissolution rate of about 500 $gm^{-2}h^{-1}$ to about 9500 $gm^{-2}h^{-1}$ or about 1000 $gm^{-2}h^{-1}$ to about 9500 $gm^{-2}h^{-1}$.

In an alternative embodiment, the substance comprising gold, palladium and/or platinum is a platinum group metal concentrate.

In an embodiment, the method further comprises:
 separating the water-miscible or partially water-miscible organic solvent containing the leached gold, palladium and/or platinum from insoluble impurities; and
 evaporating the water-miscible or partially water-miscible organic solvent from the leached gold, palladium and/or platinum.

In another embodiment, the method further comprises, after evaporating, treating the leached gold, palladium and/or platinum with a compound of Formula I:

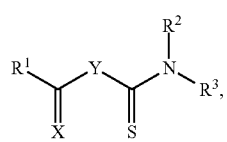

I wherein
 $R^1$ is —$NR^4R^5$ or aryl;
 $R^2$ and $R^3$ are each independently selected from H, $C_{1-10}$alkyl, $C_{3-10}$cycloalkyl, $C_{1-6}$alkylene$C_{3-10}$cycloalkyl, heterocycloalkyl and aryl; or $R^2$ and $R^3$ together with the nitrogen atom to which they are attached, form a heterocycloalkyl or a heteroaryl, or a heterocycloalkyl or a heteroaryl substituted at one or more carbon atoms with $C_{1-4}$alkyl;

$R^4$ and $R^5$ are each independently selected from H, $C_{1-10}$alkyl, $C_{3-10}$cycloalkyl, $C_{1-6}$alkylene$C_{3-10}$cycloalkyl, heterocycloalkyl and aryl; or $R^4$ and $R^5$ together with the nitrogen atom to which they are attached, form a heterocycloalkyl or a heteroaryl, or a heterocycloalkyl or a heteroaryl substituted at one or more carbon atoms with $C_{1-4}$alkyl;

X is O or S;

Y is S, $NR^6$ or $CR^6R^7$; and $R^6$ and $R^7$ are each independently selected from H, $C_{1-10}$alkyl, $C_{3-10}$cycloalkyl, $C_{1-6}$alkylene$C_{3-10}$cycloalkyl, heterocycloalkyl and aryl, under conditions to form a complex between the compound of Formula I and the leached gold and/or palladium.

In an embodiment, the compound of Formula I is a compound of Formula I (a):

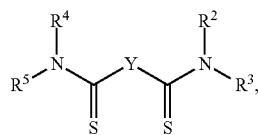

I(a)

wherein $R^2$, $R^3$, $R^4$, $R^5$ and Y are as defined for the compound of Formula I.

In an embodiment, the conditions to form the complex between the compound of Formula I and the leached gold and/or palladium comprise treating the leached gold, palladium and/or platinum with the compound of Formula I in a water-immiscible organic solvent for a time of about 2 minutes to about 30 minutes at a temperature of about 10° C. to about 40° C.

In another embodiment, the water-immiscible organic solvent is dichloromethane, chloroform, chlorobenzene or toluene.

In an embodiment, the method further comprises stripping the gold and/or palladium from the complex between the compound of Formula I and the leached gold and/or palladium by a method comprising treating the water-immiscible organic solvent containing the complex between the compound of Formula I and the leached gold and/or palladium with an aqueous solution comprising an acid and thiourea under conditions to obtain a gold and/or palladium-containing strip solution and a gold and/or palladium-reduced organic phase comprising the compound of Formula I.

In another embodiment, the method further comprises separating the gold and/or palladium-containing strip solution from the gold and/or palladium-reduced organic phase comprising the compound of Formula I and recovering gold and/or palladium from the gold and/or palladium-containing strip solution by electrowinning or reduction.

In an alternative embodiment, the method further comprises:

separating the water-miscible or partially water-miscible organic solvent containing the leached gold, palladium and/or platinum from insoluble impurities;

treating the leached gold, palladium and/or platinum in the water-miscible or partially water-miscible organic solvent with a reducing agent under conditions to obtain gold, palladium and/or platinum; and separating the gold, palladium and/or platinum from the water-miscible or partially water-miscible organic solvent.

In an embodiment, the reducing agent is selected from $NaBH_4$, ferrocene, Fe powder and Zn powder.

In another embodiment, the method further comprises recycling the water-miscible or partially water-miscible organic solvent.

In an embodiment, the method further comprises, after separating the gold, palladium and/or platinum from the water-miscible or partially water-miscible organic solvent:

dissolving the gold, palladium and/or platinum in aqua regia; and treating the dissolved gold, palladium and/or platinum with a compound of Formula I:

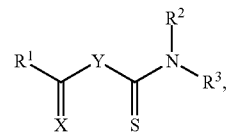

I wherein $R^1$ is $-NR^4R^5$ or aryl;

$R^2$ and $R^3$ are each independently selected from H, $C_{1-10}$alkyl, $C_{3-10}$cycloalkyl, $C_{1-6}$alkylene$C_{3-10}$cycloalkyl, heterocycloalkyl and aryl; or $R^2$ and $R^3$ together with the nitrogen atom to which they are attached, form a heterocycloalkyl or a heteroaryl, or a heterocycloalkyl or a heteroaryl substituted at one or more carbon atoms with $C_{1-4}$alkyl;

$R^4$ and $R^5$ are each independently selected from H, $C_{1-10}$alkyl, $C_{3-10}$cycloalkyl, $C_{1-6}$alkylene$C_{3-10}$cycloalkyl, heterocycloalkyl and aryl; or $R^4$ and $R^5$ together with the nitrogen atom to which they are attached, form a heterocycloalkyl or a heteroaryl, or a heterocycloalkyl or a heteroaryl substituted at one or more carbon atoms with $C_{1-4}$alkyl;

X is O or S;

Y is S, $NR^6$ or $CR^6R^7$; and $R^6$ and $R^7$ are each independently selected from H, $C_{1-10}$alkyl, $C_{3-1}$cycloalkyl, $C_{1-6}$alkylene$C_{3-10}$cycloalkyl, heterocycloalkyl and aryl, under conditions to form a complex between the compound of Formula I and the dissolved gold and/or palladium.

In an embodiment, the conditions to form the complex between the compound of Formula I and the dissolved gold and/or palladium comprise treating the dissolved gold, palladium and/or platinum with the compound of Formula I in a water-immiscible organic solvent for a time of about 2 minutes to about 30 minutes at a temperature of about 10° C. to about 40° C.

In another embodiment, the water-immiscible organic solvent is dichloromethane, chloroform, chlorobenzene or toluene.

In an embodiment, the method further comprises stripping the gold and/or palladium from the complex between the compound of Formula I and the dissolved gold and/or palladium by a method comprising contacting the water-immiscible organic solvent containing the complex between the compound of Formula I and the dissolved gold and/or palladium with an aqueous solution comprising an acid and thiourea under conditions to obtain a gold and/or palladium-containing strip solution and a gold and/or palladium-reduced organic phase comprising the compound of Formula I.

In another embodiment, the method further comprises separating the gold and/or palladium-containing strip solution from the gold and/or palladium-reduced organic phase comprising the compound of Formula I and recovering gold and/or palladium from the gold and/or palladium-containing strip solution by electrowinning or reduction.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The present application will now be described in greater detail with reference to the drawings in which.

DETAILED DESCRIPTION

I. Definitions

Figure 1:
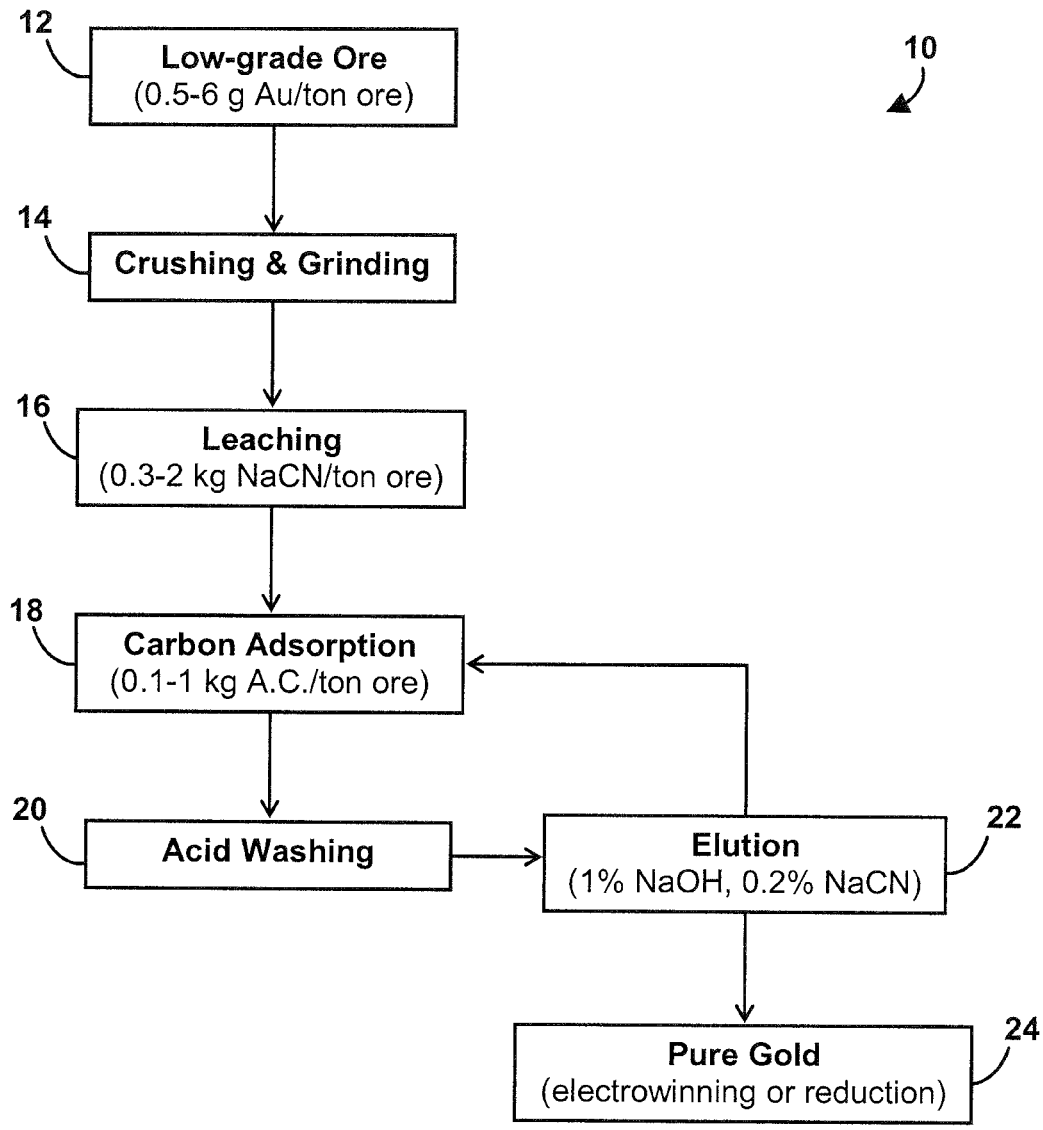
FIG. 1 shows a schematic representation of a process of gold recovery using cyanide leaching according to the prior art.

Unless otherwise indicated, the definitions and embodiments described in this and other sections are intended to be applicable to all embodiments and aspects of the present application herein described for which they are suitable as would be understood by a person skilled in the art.

The term "compound of the present application" and the like as used herein refers to a compound of Formula I as defined herein.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In embodiments of the present application, the compounds described herein have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers or racemic mixtures thereof are included within the scope of the present application.

The term "suitable" as used herein means that the selection of specific reagents or conditions will depend on the reaction being performed and the desired results, but nonetheless, can generally be made by a person skilled in the art once all relevant information is known.

The term "immiscible" as used herein when referring to two liquid phases means that the two liquid phases cannot be mixed to form a solution having a single phase under the conditions used, such as the relative proportions of the two liquid phases and/or the temperature, etc. Two immiscible liquid phases will, for example separate into two liquid phases after mixing. Each of these two liquid phases may, for example contain small amounts of the other liquid phase. Accordingly, a "water-immiscible" liquid such as a "water-immiscible organic solvent" is a liquid that cannot be mixed with water to form a solution having a single phase under the conditions used but that may, for example contain small amounts of water after being mixed with water.

The term "partially miscible" as used herein when referring to two liquid phases means that the two liquid phases will, for example, separate into two liquid phases after mixing, each liquid phase containing a portion of the other liquid phase in a dissolved state. Accordingly, a "partially water-miscible organic solvent" is a liquid that, after mixing with water, will separate into two liquid phases after mixing, one phase being water containing a portion, for example, about 10% (v/v) of the partially water-miscible organic liquid in a dissolved state, and the other phase being the partially water-miscible organic liquid containing a portion, for example, about 10% (v/v) of water in a dissolved state.

The term "miscible" as used herein when referring to two liquid phases means that the two liquid phases can, for example be mixed in all proportions to form a homogeneous solution. Two miscible liquid phases will not, for example separate into two liquid phases after mixing. Accordingly, a "water-miscible" liquid such as a "water-miscible organic solvent" is a liquid that can be mixed with water to form a homogeneous solution.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-10}$alkyl means an alkyl group having 1, 2, 3, 4, 5, 6, 7, 8, 9 or 10 carbon atoms.

The term "alkylene" as used herein, whether it is used alone or as part of another group, means straight or branched chain, saturated alkylene group, that is, a saturated carbon chain that contains substituents on two of its ends. The number of carbon atoms that are possible in the referenced alkylene group are indicated by the numerical prefix "$C_{n1-n2}$". For example, the term $C_{1-6}$alkylene means an alkylene group having 1, 2, 3, 4, 5 or 6 carbon atoms.

The term "cycloalkyl," as used herein, whether it is used alone or as part of another group, means saturated alkyl groups having at least one cyclic ring. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "heterocycloalkyl" as used herein, whether it is used alone or as part of another group, refers to a non-aromatic, ring-containing group having one or more multivalent heteroatoms, independently selected from N, O and S, as a part of the ring structure and including at least 3 and up to 20 atoms in the ring(s). Heterocycloalkyl groups are either saturated or unsaturated (i.e. contain one or more double bonds) and may contain more than one ring.

The term "aryl" as used herein, whether it is used alone or as part of another group, refers to cyclic groups that contain at least one aromatic ring. In an embodiment of the application, the aryl group contains from 6, 9, 10 or 14 atoms, such as phenyl, naphthyl, indanyl or anthracenyl.

The term "heteroaryl" as used herein, whether it is used alone or as part of another group, refers to an aromatic, ring-containing group having one or more multivalent heteroatoms, independently selected from N, O and S, as a part of the ring structure and including at least 5 and up to 20 atoms in the ring(s). Heteroaryl groups may contain more than one ring.

II. Methods of the Application

The present studies disclose the use of a polar, water-miscible or partially water-miscible organic solvent in combination with conventional leaching reagents. Conventional leaching reagents, for example, acidified chloride solutions containing an oxidizing agent have not been investigated for gold leaching directly in organic solvents. A number of leaching reagents were investigated in the present studies. Using mixtures of HCl with $H_2O_2$ or $Ca(ClO)_2$ in ethyl acetate or acetonitrile achieved greater than 99.9% gold leaching in a short period of time with 1M HCl using a very low concentration of the oxidant. The results show that these new leaching systems can dissolve gold much more rapidly than even aqua regia despite the relevant concentrations of leaching materials being much lower. The leached gold can then be precipitated out from the ethyl acetate or acetonitrile solution, for example, by direct reduction of $AuCl_4^-$ by $NaBH_4$, zinc or ferrocene. Because some other impurities can be reduced during gold reduction, the resulting gold precipitate can then be purified by solvent extraction using, for example a compound of Formula I as defined herein. In some embodiments, this new recovery system, for example, simplifies the recovery process, saves considerable time and energy and due, to the recoverability of the organic solvent, produces less waste.

Accordingly, the present application includes a method of leaching gold, palladium and/or platinum from a substance comprising gold, palladium and/or platinum, the method comprising contacting the substance with a mixture comprising:
  (a) an acid;
  (b) an oxidizing agent; and
  (c) a water-miscible or partially water-miscible organic solvent, under conditions to leach the gold, palladium and/or platinum from the substance.

In an embodiment, the method further comprises:
  separating the water-miscible or partially water-miscible organic solvent containing the leached gold, palladium and/or platinum from insoluble impurities; and
  evaporating the water-miscible or partially water-miscible organic solvent from the leached gold, palladium and/or platinum.

The water-miscible or partially water-miscible organic solvent containing the leached gold, palladium and/or platinum and the insoluble impurities are separated by any suitable means, the selection of which can be made by a person skilled in the art.

The water-miscible or partially water-miscible organic solvent is evaporated from the leached gold, palladium and/or platinum by any suitable means, the selection of which can be made by a person skilled in the art. In an embodiment, distillation is used for evaporating the water-miscible or partially water-miscible organic solvent from the leached gold, palladium and/or platinum.

In another embodiment, the method further comprises, after evaporating, treating the leached gold, palladium and/or platinum with a compound of Formula I:

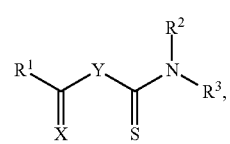

wherein
  $R^1$ is —$NR^4R^5$ or aryl;
  $R^2$ and $R^3$ are each independently selected from H, $C_{1-10}$alkyl, $C_{3-10}$cycloalkyl, $C_{1-6}$alkylene$C_{3-10}$cycloalkyl, heterocycloalkyl and aryl; or $R^2$ and $R^3$ together with the nitrogen atom to which they are attached, form a heterocycloalkyl or a heteroaryl, or a heterocycloalkyl or a heteroaryl substituted at one or more carbon atoms with $C_{1-4}$alkyl;

$R^4$ and $R^5$ are each independently selected from H, $C_{1-10}$alkyl, $C_{3-10}$cycloalkyl, $C_{1-6}$alkylene$C_{3-10}$cycloalkyl, heterocycloalkyl and aryl; or $R^4$ and $R^5$ together with the nitrogen atom to which they are attached, form a heterocycloalkyl or a heteroaryl, or a heterocycloalkyl or a heteroaryl substituted at one or more carbon atoms with $C_{1-4}$alkyl;

X is O or S;

Y is S, $NR^6$ or $CR^6R^7$; and $R^6$ and $R^7$ are each independently selected from H, $C_{1-10}$alkyl, $C_{3-10}$cycloalkyl, $C_{1-6}$alkylene$C_{3-10}$cycloalkyl, heterocycloalkyl and aryl, under conditions to form a complex between the compound of Formula I and the leached gold and/or palladium. Under such conditions, platinum does not, for example, form a complex with the compound of Formula I.

In an embodiment, $R^1$ is $-NR^4R^5$.

In an alternative embodiment, $R^1$ is aryl. In another embodiment, $R^1$ is $C_{6-10}$aryl. In a further embodiment, $R^1$ is phenyl.

In another embodiment, the compound of Formula I is a compound of Formula I (a):

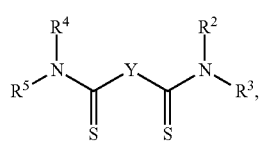

wherein $R^2$, $R^3$, $R^4$, $R^5$ and Y are as defined for the compound of Formula I.

In an embodiment of the present application, for example, in the compound of Formula I (a), only one of $R^2$, $R^3$, $R^4$ and $R^5$ is H.

In another embodiment of the present application, for example, in the compound of Formula I (a), $R^2$ and $R^3$ together with the nitrogen atom to which they are attached, form a heterocycloalkyl, a heteroaryl or a substituted heterocycloalkyl or a substituted heteroaryl.

In an embodiment, for example, in the compound of Formula I (a), $R^2$ and $R^3$ together with the nitrogen atom to which they are attached form a heterocycloalkyl or a substituted heterocycloalkyl. In another embodiment, example, in the compound of Formula I (a), $R^2$ and $R^3$ together with the nitrogen atom to which they are attached form a heterocycloalkyl or a substituted heterocycloalkyl, wherein heterocycloalkyl is selected from aziridinyl, azetidinyl, pyrrolidinyl, piperidinyl, azepanyl, azocanyl, imidazolidinyl, oxazolidinyl, thiazolidinyl, piperazinyl, hexahydropyrimidinyl, morpholinyl, 1,3-oxazinanyl, thiomorpholinyl, 1,3-thiazinanyl, 1,3-diazepanyl, 1,3-oxazepanyl, 1,3-thiazepanyl, 1,4-diazepanyl, 1,4-oxazepanyl, 1,4-thiazepanyl, 1,3-diazocanyl, 1,3-oxazocanyl, 1,3-thiazocanyl, 1,4-diazocanyl, 1,4-oxazocanyl, 1,4-thiazocanyl, 1,5-diazocanyl, 1,5-oxazocanyl and 1,5-thiazocanyl. In a further embodiment, for example, in the compound of Formula I (a), $R^2$ and $R^3$ together with the nitrogen atom to which they are attached form morpholinyl, pyrrolidinyl or 4-methylpiperidinyl. In an embodiment, for example, in the compound of Formula I (a), $R^2$ and $R^3$ together with the nitrogen atom to which they are attached form morpholinyl. In another embodiment, for example, in the compound of Formula I (a), $R^2$ and $R^3$ together with the nitrogen atom to which they are attached form pyrrolidinyl. In a further embodiment, for example, in the compound of Formula I (a), $R^2$ and $R^3$ together with the nitrogen atom to which they are attached form 4-methylpiperidinyl.

In an embodiment, for example, in the compound of Formula I (a), $R^2$ and $R^3$ together with the nitrogen atom to which they are attached form a heteroaryl or a substituted heteroaryl. In another embodiment of the present application, for example, in the compound of Formula I (a), $R^2$ and $R^3$ together with the nitrogen atom to which they are attached form a heteroaryl. In a further embodiment, for example, in the compound of Formula I (a), $R^2$ and $R^3$ together with the nitrogen atom to which they are attached form a heteroaryl selected from pyrrolyl, imidazolyl, pyrazolyl, oxazolyl, isoxazolyl, thiazolyl, isothiazolyl, 1,2,3-triazolyl, 1,2,4-triazolyl, furazanyl, pyridinyl, pyrazinyl, pyrimidinyl, pyridazinyl, 1,2,3-triazinyl, 1,2,4-triazinyl and 1,3,5-triazinyl.

In an embodiment, for example, in the compound of Formula I (a), $R^4$ is selected from H, $C_{3-10}$cycloalkyl, $C_{1-8}$alkylene$C_{3-10}$cycloalkyl, heterocycloalkyl and aryl. In another embodiment, for example, in the compound of Formula I (a), $R^4$ is selected from H, $C_{1-8}$alkyl, $C_{3-8}$cycloalkyl, $C_{1-4}$alkylene$C_{3-8}$cycloalkyl, heterocycloalkyl and phenyl. In a further embodiment, for example, in the compound of Formula I (a), $R^4$ is selected from H, $C_{1-8}$alkyl and $C_{3-8}$cycloalkyl. It is an embodiment that, for example, in the compound of Formula I (a), $R^4$ is selected from H and $C_{1-4}$alkyl. In another embodiment of the present application, for example, in the compound of Formula I (a), $R^4$ is H.

In an embodiment, for example, in the compound of Formula I (a), $R^5$ is selected from H, $C_{3-10}$cycloalkyl, $C_{1-8}$alkylene$C_{3-10}$cycloalkyl, heterocycloalkyl and aryl. In another embodiment, for example, in the compound of Formula I (a), $R^5$ is selected from $C_{3-10}$alkyl, $C_{3-8}$cycloalkyl, $C_{1-4}$alkylene$C_{3-8}$cycloalkyl, heterocycloalkyl and phenyl. In a further embodiment, for example, in the compound of Formula I (a), $R^5$ is selected from $C_{1-8}$alkyl and $C_{3-8}$cycloalkyl. It is an embodiment, for example, in the compound of Formula I (a), that $R^5$ is isopropyl or cyclohexyl. In another embodiment, for example, in the compound of Formula I (a), $R^5$ is isopropyl. In a further embodiment, for example, in the compound of Formula I (a), $R^5$ is cyclohexyl.

In an embodiment, at least one of any one of $R^1$ to $R^7$ is aryl. In another embodiment, at least one of any one of $R^1$ to $R^7$ is phenyl.

In an embodiment, for example, in the compound of Formula I (a), $R^4$ is H or $C_{1-4}$alkyl and $R^5$ is $C_{1-6}$alklyl or $C_{3-8}$cycloalkyl. In another embodiment, for example, in the compound of Formula I (a), $R^4$ is H and $R^5$ is $C_{1-6}$alkyl or $C_{3-8}$cycloalkyl. In a further embodiment of the present application, for example, in the compound of Formula I (a), $R^4$ is H and $R^5$ is $C_{1-6}$alkyl. It is an embodiment, for example, in the compound of Formula I (a), that $R^4$ is H and $R^5$ is $C_{3-8}$cycloalkyl. In another embodiment, for example, in the compound of Formula I (a), $R^4$ is H and $R^5$ is isopropyl. In a further embodiment, for example, in the compound of Formula I (a), $R^4$ is H and $R^5$ is cyclohexyl.

In an embodiment, X is O. In another embodiment, X is S.

In an embodiment, Y is $NR^6$.

In an embodiment, $R^6$ is selected from H, $C_{1-10}$alkly, $C_{3-10}$cycloalkyl, $C_{1-6}$alkylene$C_{3-10}$cycloalkyl, heterocycloalkyl and aryl. In another embodiment, $R^6$ is selected from H, $C_{1-6}$alkyl, $C_{3-8}$cycloalkyl, $C_{1-4}$alkylene$C_{3-8}$cycloalkyl and heterocycloalkyl. In a further embodiment, $R^6$ is H, $C_{1-6}$alkyl or $C_{3-8}$cycloalkyl. It is an embodiment that $R^6$ is H. In another embodiment $R^6$ is $C_{1-6}$alkyl. In another embodiment of the present application, $R^6$ is $C_{3-8}$cycloalkyl. In a further embodiment, $R^6$ is isopropyl. It is an embodiment that $R^6$ is cyclohexyl.

In an embodiment, Y is $CR^6R^7$.

In an embodiment, $R^6$ and $R^7$ are each independently selected from H, $C_{1-10}$alkly, $C_{3-10}$cycloalkyl, $C_{1-6}$alkylene$C_{3-10}$cycloalkyl, heterocycloalkyl and aryl. In another embodiment, $R^6$ and $R^7$ are each independently selected from H, $C_{1-6}$alkyl, $C_{3-8}$cycloalkyl, $C_{1-4}$alkylene$C_{3-8}$cycloalkyl and heterocycloalkyl. In a further embodiment, $R^6$ and $R^7$ are each independently H, $C_{1-6}$alkyl or $C_{3-8}$cycloalkyl.

In an embodiment, the compound of Formula I is a compound of Formula I (a)(i), I (a)(ii), I (a)(iii) or I (a)(iv):

In another embodiment of the present application, the compound of Formula I is the compound of Formula I (a)(i):

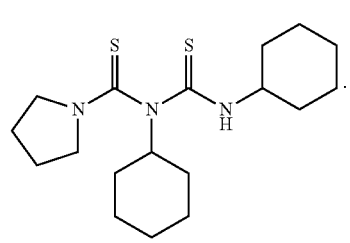

I(a)(i)

In another embodiment of the present application, the compound of Formula I is the compound of Formula I (a)(ii):

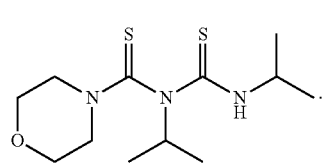

I(a)(ii)

In another embodiment of the present application, the compound of Formula I is the compound of Formula I (a)(iii):

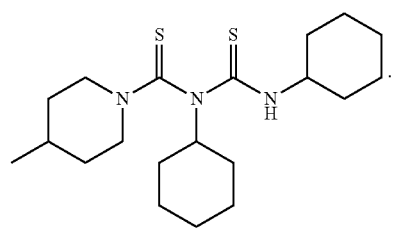

I(a)(iii)

In another embodiment of the present application, the compound of Formula I is the compound of Formula I (a)(iv):

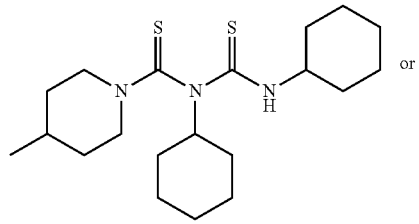

I(a)(ii)

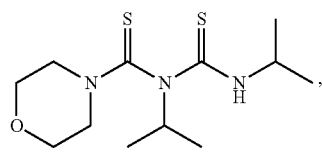

I(a)(iii) or

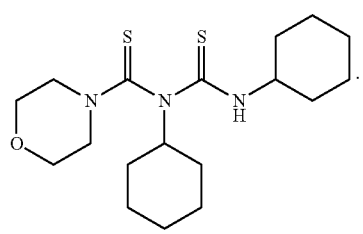

I(a)(iv)

In another embodiment, the compound of Formula I is a compound of Formula I (b)(i):

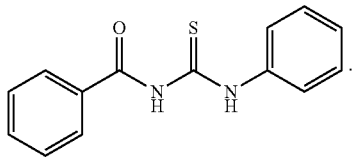

I(b)(i)

In another embodiment, the compound of Formula I is a compound of Formula I (c)(i), I (c)(ii), I (c)(iii) or I (c)(iv):

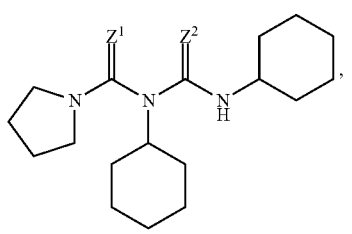

I(c)(i)

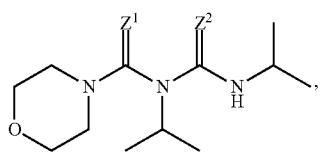

I(c)(ii)

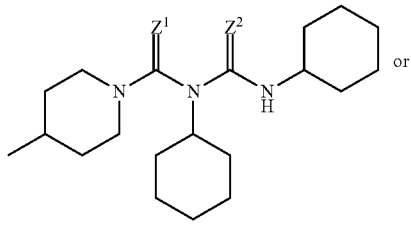

I(c)(iii)

or

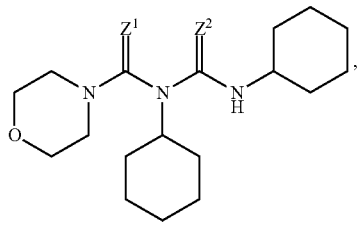

I(c)(iv)

wherein in each of the compounds of Formula I (c)(i), I (c)(ii), I (c)(iii) or I (c)(iv) independently, one of $Z^1$ and $Z^2$ is O and the other of $Z^1$ and $Z^2$ is S.

In an embodiment, the compounds of Formula I are commercially available or are prepared using methods known in the literature from commercially available materials. For example, a compound of Formula I (a) is prepared by adding an appropriately substituted amine to a mixture of $CS_2$ and a carbodiimide in a suitable polar solvent, such as an alcoholic solvent, under conditions to form the compound of Formula I (a). The compound of Formula I (a) will generally precipitate from the reaction mixture and is isolated and, optionally, purified using known methods. In an embodiment, a slight excess, for example 1.05 to 1.5, suitably 1.1, equivalents of the amine and $CS_2$ are used. In an embodiment, the suitable solvent is methanol or ethanol, suitably methanol. In an embodiment the reaction is performed at or around room temperature, however the temperature can be adjusted as needed by a person skilled in the art.

In an embodiment, the conditions to form the complex between the compound of Formula I and the leached gold and/or palladium comprise treating the leached gold, palladium and/or platinum with the compound of Formula I in a water-immiscible organic solvent for a time of about 2 minutes to about 30 minutes at a temperature of about 10° C. to about 40° C. It will be appreciated by a person skilled in the art that platinum remains in the aqueous phase and is not extracted to the organic phase by the compound of Formula I. Platinum can be recovered from the aqueous phase by any suitable method, the selection of which can be made by a person skilled in the art.

In an embodiment, the molar ratio of the compound of Formula I to the gold and/or palladium is about 1:10 to about 50:1. In another embodiment, the molar ratio of the compound of Formula I to the gold and/or palladium is about 1:1 to about 20:1. In a further embodiment, the molar ratio of the compound of Formula I to the gold and/or palladium is about 2:1 to about 10:1. It is an embodiment that the molar ratio of the compound of Formula I to the gold and/or palladium is about 3:1 to about 4:1. In another embodiment, the molar ratio of the compound of Formula I to the gold and/or palladium is about 3:1. In a further embodiment, the molar ratio of the compound of Formula I to the gold and/or palladium is about 4:1.

In an embodiment, the water-immiscible organic solvent is dichloromethane, chloroform, chlorobenzene or toluene. In another embodiment, the water-immiscible organic solvent is dichloromethane.

In another embodiment, the method further comprises stripping the gold and/or palladium from the complex between the compound of Formula I and the leached gold and/or palladium by a method comprising treating the water-immiscible organic solvent containing the complex between the compound of Formula I and the leached gold and/or palladium with an aqueous solution comprising an acid and thiourea under conditions to obtain a gold and/or palladium-containing strip solution and a gold and/or palladium-reduced organic phase comprising the compound of Formula I. In an embodiment, the conditions to obtain a gold and/or palladium-containing strip solution and a gold and/or palladium-reduced organic phase comprise stirring the water-immiscible organic solvent with an aqueous solution comprising $H_2SO_4$, for example 1M $H_2SO_4$ and thiourea, for example 0.7 M thiourea for a time of about 5 minutes to about 1 hour or about 15 minutes at a temperature of about 10° C. to about 40° C. or about 20° C. to about 25° C. Other suitable acids such as but not limited to HCl may be used in the stripping step. However, it will be appreciated by a person skilled in the art that HCl is corrosive and that HCl gas may come out from the solution during subsequent reduction or electrowinning.

In a further embodiment, the method further comprises separating the gold and/or palladium-containing strip solution from the gold and/or palladium-reduced organic phase comprising the compound of Formula I and recovering gold and/or palladium from the gold and/or palladium-containing strip solution by electrowinning or reduction. The gold and/or palladium-containing strip solution and the gold and/or palladium-reduced organic phase comprising the compound of Formula I are separated by any suitable means, the selection of which for use in the methods of the present application can be made by a person skilled in the art.

In an alternative embodiment, the method further comprises:

separating the water-miscible or partially water-miscible organic solvent containing the leached gold, palladium and/or platinum from insoluble impurities;

treating the leached gold, palladium and/or platinum in the water-miscible or partially water-miscible organic solvent with a reducing agent under conditions to obtain gold, palladium and/or platinum; and separating the gold, palladium and/or platinum from the water-miscible or partially water-miscible organic solvent.

The water-miscible or partially water-miscible organic solvent containing the leached gold, palladium and/or platinum and the insoluble impurities are separated by any suitable means, the selection of which can be made by a person skilled in the art. The gold, palladium and/or platinum and the water-miscible or partially water-miscible organic solvent are separated by any suitable means, the selection of which can be made by a person skilled in the art.

The reducing agent can be any suitable reducing agent. In an embodiment of the present application, the reducing agent is selected from $NaBH_4$, ferrocene, Fe powder and Zn powder.

In another embodiment, the method further comprises recycling the water-miscible or partially water-miscible organic solvent.

In an embodiment, the method further comprises, after separating the gold, palladium and/or platinum from the water-miscible or partially water-miscible organic solvent:

dissolving the gold, palladium and/or platinum in aqua regia; and treating the dissolved gold, palladium and/or platinum with a compound of Formula I:

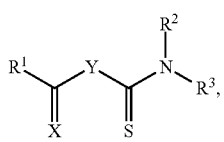

wherein $R^1$ is —$NR^4R^5$ or aryl;

$R^2$ and $R^3$ are each independently selected from H, $C_{1-10}$alkyl, $C_{3-10}$cycloalkyl, $C_{1-6}$alkylene$C_{3-10}$cycloalkyl, heterocycloalkyl and aryl; or $R^2$ and $R^3$ together with the nitrogen atom to which they are attached, form a heterocycloalkyl or a heteroaryl, or a heterocycloalkyl or a heteroaryl substituted at one or more carbon atoms with $C_{1-4}$alkyl;

$R^4$ and $R^5$ are each independently selected from H, $C_{1-10}$alkyl, $C_{3-10}$cycloalkyl, $C_{1-6}$alkylene$C_{3-10}$cycloalkyl, heterocycloalkyl and aryl; or $R^4$ and $R^5$ together with the nitrogen atom to which they are attached, form a heterocycloalkyl or a heteroaryl, or a heterocycloalkyl or a heteroaryl substituted at one or more carbon atoms with $C_{1-4}$alkyl;

X is O or S;

Y is S, $NR^6$ or $CR^6R^7$; and $R^6$ and $R^7$ are each independently selected from H, $C_{1-10}$alkyl, $C_{3-10}$cycloalkyl, $C_{1-6}$alkylene$C_{3-10}$cycloalkyl, heterocycloalkyl and aryl, under conditions to form a complex between the compound of Formula I and the dissolved gold and/or palladium. Under such conditions, platinum does not, for example, form a complex with the compound of Formula I. The compound of Formula I can be varied as detailed herein.

In another embodiment, the conditions to form the complex between the compound of Formula I and the dissolved gold and/or palladium comprise treating the dissolved gold, palladium and/or platinum with the compound of Formula I in a water-immiscible organic solvent for a time of about 2 minutes to about 30 minutes at a temperature of about 10° C. to about 40° C. It will be appreciated by a person skilled in the art that platinum remains in the aqueous phase and is not extracted to the organic phase by the compound of Formula I. Platinum can be recovered from the aqueous phase by any suitable method, the selection of which can be made by a person skilled in the art.

In an embodiment, the water-immiscible organic solvent is dichloromethane, chloroform, chlorobenzene or toluene. In another embodiment, the water-immiscible organic solvent is dichloromethane.

In an embodiment, the method further comprises stripping the gold and/or palladium from the complex between the compound of Formula I and the dissolved gold and/or palladium by a method comprising contacting the water-immiscible organic solvent containing the complex between the compound of Formula I and the dissolved gold and/or palladium with an aqueous solution comprising an acid and thiourea under conditions to obtain a gold and/or palladium-containing strip solution and a gold and/or palladium-reduced organic phase comprising the compound of Formula I. In an embodiment, the conditions to obtain a gold and/or palladium-containing strip solution and a gold and/or palladium-reduced organic phase comprise stirring the water-immiscible organic solvent with an aqueous solution comprising $H_2SO_4$, for example 1M $H_2SO_4$ and thiourea, for example 0.7 M thiourea for a time of about 5 minutes to about 1 hour or about 15 minutes at a temperature of about 10° C. to about 40° C. or about 20° C. to about 25° C. Other suitable acids such as but not limited to HCl may be used in the stripping step. However, it will be appreciated by a person skilled in the art that HCl is corrosive and that HCl gas may come out from the solution during subsequent reduction or electrowinning.

In another embodiment, the method further comprises separating the gold and/or palladium-containing strip solution from the gold and/or palladium-reduced organic phase comprising the compound of Formula I and recovering gold and/or palladium from the gold and/or palladium-containing strip solution by electrowinning or reduction. The gold and/or palladium-containing strip solution and the gold and/or palladium-reduced organic phase comprising the compound of Formula I are separated by any suitable means, the selection of which for use in the methods of the present application can be made by a person skilled in the art.

In an embodiment, the gold and/or palladium is recovered from the gold and/or palladium-containing strip solution by electrowinning.

In another embodiment, the gold and/or palladium is recovered from the gold and/or palladium-containing strip solution by reduction. The reducing agent can be any suitable reducing agent. In an embodiment, the reducing agent is oxalic acid, Zn powder, Fe powder or $NaBH_4$. In an embodiment, the reducing agent is $NaBH_4$ and a temperature of from about 10° C. to about 35° C. or about 20° C. to about 25° C. is used. In another embodiment, the reducing agent is oxalic acid and a temperature of from about 40° C. to about 60° C. or about 50° C. is used.

In an embodiment, the conditions to leach the gold, palladium and/or platinum from the gold, palladium and/or platinum-containing substance comprise stirring the gold, palladium and/or platinum-containing substance and the mixture for a time of about 0.1 minute to about 4 hours, about 0.1 minute to about 2 hours, about 0.1 minute to about 30 minutes or less than about 15 minutes at a temperature of about 10° C. to about 80° C., about 10° C. to about 40° C. or about 20° C. to about 25° C.

The acid in the mixture can be any suitable acid; i.e. the acid in the mixture can be any suitable proton donor. In an embodiment, the acid is a hydrogen halide (e.g., HCl, HBr or HI), chlorous acid, chloric acid, bromous acid, bromic acid, iodous acid, iodic acid, perchloric acid, sulfuric acid, nitric acid, oxalic acid, phosphoric acid, an organic acid (e.g., benzenesulfonic acid) or combinations thereof. In an embodiment, the acid is selected from HCl, $H_2SO_4$, HBr, $HNO_3$, $H_3PO_4$ and HI. In another embodiment, the acid is selected from HCl, $H_2SO_4$, HBr and HI. In another embodiment, the acid is HCl. The concentration of the acid can be any suitable concentration. In an embodiment, the acid is an aqueous solution of HCl having a concentration of from about 0.01 M to about 4 M. In a further embodiment, the acid is an aqueous solution of HCl having a concentration of from about 0.5 M to about 4 M. It is an embodiment that the acid is an aqueous solution of HCl having a concentration of from about 1 M to about 2.5 M, about 0.1 M to about 2.5 M or about 0.01 M to about 2.5 M. In another embodiment, the acid is an aqueous solution of HCl having a concentration of about 2 M. In a further embodiment of the present application, the acid is an aqueous solution of HCl having a concentration of about 1 M.

The oxidizing agent in the mixture can be any suitable oxidizing agent. In an embodiment, the oxidizing agent is ozone, nitric acid ($HNO_3$), hydrogen peroxide ($H_2O_2$), $O_2$, bubbled air, $I_2$, $Br_2$, $Cl_2$, OXONE™ (potassium monopersulfate), an ammonium polyatomic salt (e.g., ammonium chlorite, ammonium periodate ($NH_4IO_3$), ammonium perborate ($NH_4BO_3$), ammonium chlorate ($NH_4ClO_3$), ammonium persulfate ($(NH_4)_2S_2O_8$), ammonium hypochlorite or ammonium nitrate), calcium hypochlorite, a sodium polyatomic salt (e.g., sodium persulfate ($Na_2S_2O_8$), sodium nitrate or sodium hypochlorite), a potassium polyatomic salt (e.g., potassium permanganate, potassium persulfate, potassium iodate, potassium hypochlorite or potassium nitrate), manganese oxide, a tetraalkylammonium salt (e.g., tetramethylammonium chlorite ($N(NH_3)_4)ClO_2$) or tetramethylammonium periodate ($N(NH_3)_4)IO_4$)), peroxomonosulfuric acid, urea, peracetic acid, an alkanesulfonic acid (e.g., methane sulfonic acid), an aromatic sulfonic acid (e.g., benzenesulfonic acid) or combinations thereof. In another embodiment, the oxidizing agent is selected from $H_2O_2$, $Cl_2$, $Br_2$, $I_2$, $Ca(ClO)_2$, $HNO_3$, $MnO_2$, $KMnO_4$ and $K_2Cr_2O_7$. In another embodiment, the oxidizing agent is $H_2O_2$ or $Ca(CiO)_2$. In a further embodiment, the oxidizing agent is $H_2O_2$. It is an embodiment that the oxidizing agent is $Ca(ClO)_2$. The concentration of the oxidizing agent can be any suitable concentration. For example, water may decrease the leaching efficiency in the methods of leaching gold from a gold-containing substance of the present application. In another embodiment, the oxidizing agent is an aqueous solution of $H_2O_2$ having a concentration of from about 0.01 M to about 1.0 M. In a further embodiment, the oxidizing agent is an aqueous solution of $H_2O_2$ having a concentration of from about 0.05 M to about 0.5 M. It is an embodiment that the oxidizing agent is an aqueous solution of $H_2O_2$ having a concentration of from about 0.1 M to about 0.3 M. In another embodiment, the oxidizing agent is an aqueous solution of $CaClO_2$ having a concentration of from about 0.005 M to about 0.5 M. In a further embodiment, the oxidizing agent is an aqueous solution of $CaClO_2$ having a concentration of from about 0.01 M to about 0.2 M. It is an embodiment that the oxidizing agent is an aqueous solution of $CaClO_2$ having a concentration of from about 0.03 M to about 0.1 M.

The water-miscible or partially water-miscible organic solvent can be any suitable water-miscible or partially water-miscible organic solvent including organic acids such as acetic acid. In an embodiment, the water-miscible or partially water-miscible organic solvent in the mixture is selected from acetic acid, ethyl acetate, acetonitrile, tetrahydrofuran (THF), dimethylformamide (DMF), dimethyl sulfoxide (DMSO) and methanol (MeOH). In another embodiment, the water-miscible or partially water-miscible organic solvent is selected from acetic acid, ethyl acetate, acetonitrile and THF. In a further embodiment, the water-miscible or partially water-miscible organic solvent is selected from acetic acid, ethyl acetate and acetonitrile. In another embodiment, the water-miscible or partially water-miscible organic solvent is ethyl acetate or acetonitrile. It is an embodiment that the water-miscible or partially water-miscible organic solvent comprises, consists essentially of or consists of ethyl acetate. In another embodiment, the water-miscible or partially water-miscible organic solvent comprises, consists essentially of or consists of acetonitrile. In a further embodiment, the water-miscible or partially water-miscible organic solvent comprises, consists essentially of or consists of acetic acid.

In an embodiment, the mixture further comprises a metal halide, an ammonium halide or a tetraalkylammonium halide, or a combination thereof. In an embodiment, mixture comprises a metal halide and the metal halide is an alkali metal halide, an alkaline earth metal halide or an aluminium halide, or a combination thereof. In an embodiment, the metal halide is sodium halide, potassium halide, lithium halide, calcium halide, magnesium halide or aluminum halide, or a combination thereof. In an embodiment, the tetraalkylammonium halide is a tetra($C_{1-4}$alkyl)ammonium halide, such as tetramethylammonium chloride. In an embodiment, the ammonium halide is ammonium bromide or ammonium chloride, or a combination thereof. In another embodiment of the present application, the mixture further comprises a reagent selected from NaCl, KCl, NaBr, KBr, NaI, KI, $CaCl_2$, $MgCl_2$, $NH_4Br$, $NH_4Cl$ and $N(CH_3)_4Cl$, or a combination thereof. In a further embodiment, the mixture further comprises the metal halide and the metal halide is $CaCl_2$, It is an embodiment that the $CaCl_2$ in the mixture has a concentration of about 0.05M to about 1.5M, about 0.3M to about 0.8M or about 0.6M. In another embodiment, reagent (a) in the mixture is HCl, reagent (b) in the mixture is $H_2O_2$ and reagent (c) in the mixture is acetic acid.

The substance comprising gold, palladium and/or platinum can be any suitable substance comprising gold, palladium and/or platinum. In an embodiment, the substance comprising gold, palladium and/or platinum is selected from a gold-containing ore, anode slime, a platinum group metal (PGM)-containing substance such as a PGM concentrate, electronic scrap and jewelry scrap.

In an embodiment, the substance comprising gold and/or palladium is a gold-containing substance. In another embodiment of the present application, the gold-containing substance is a gold-containing ore. In another embodiment of the present application, the gold ore is an oxidized gold ore. In another embodiment, the gold ore is a refractory gold ore.

In an embodiment, the gold-containing substance further comprises iron, copper, cobalt, or nickel or a combination thereof, and the method selectively dissolves the gold from the gold-containing substance.

In an embodiment, the method provides a gold dissolution rate of at least 500 $gm^{-2}h^{-1}$, at least 1000 $gm^{-2}h^{-1}$ or at least 5000 $gm^{-2}h^{-1}$. In another embodiment, the method provides a gold dissolution rate of about 500 $gm^2h'$ to about 9500 $gm^{-2}h^{-1}$ or about 1000 $gm^{-2}h^{-1}$ to about 9500 $gm^{-2}h_{31\ 1}$.

In an embodiment, the substance comprising gold, palladium and/or platinum is a palladium-containing substance. In another embodiment of the present application, the palladium-containing substance is a palladium-containing ore. In an embodiment, the substance comprising gold, palladium and/or platinum is a platinum-containing substance. In another embodiment of the present application, the platinum-containing substance is a platinum-containing ore.

In an embodiment, the substance comprising gold, palladium and/or platinum is a platinum group metal-containing substance. In another embodiment, the platinum group metal-containing substance is a platinum group metal concentrate. It will be appreciated by a person skilled in the art that after dissolution of substances containing platinum group metals including platinum, palladium, rhodium, osmium, ruthenium and iridium the compounds of Formula I can selectively extract both palladium and gold into the organic phase and separate them from the rest of the platinum group metals.[49]

In another embodiment of the present application, the method comprises crushing and/or grinding the substance comprising gold, palladium and/or platinum such as the gold-containing ore into particles prior to contacting with the mixture. In a further embodiment, the size of the particles of the substance comprising gold, palladium and/or platinum such as the gold-containing ore is less than or equal to about 75 microns.

The following non-limiting examples are illustrative of the present application:

EXAMPLES

Example 1

New Leaching Methods Employing Sulfur-Based Ligands for Selective Extraction and Recovery of Gold General Ligand Syntheses The ligands I (a)(i), I (a)(ii), I (a)(iii) and I (a)(iv) (Scheme 2) used in this research were synthesized by following reported literature procedures.[49] The ligand I (b)(i) (N-phenyl-N'-benzoylthiourea) was synthesized based on a reported procedure.[50]

For example, for ligands I (a)(i)-I (a)(iv), in a round bottom flask, 1.1 equivalents of a substituted amine was added in small portions over a period of 1 hour to a mixture of 1.3 equivalents of $CS_2$ and 1 equivalent of carbodiimide in methanol at room temperature. The reaction mixture was stirred for 4 hours, and then the resulting white precipitate was separated from the solution by filtration. Finally, it was washed with water and dried under vacuum.

Ligand $L_1$ Synthesis

In a round bottom flask, 2.02 g pyrrolidine was added in small portions over a period of 1 hour to a mixture of 2.80 g $CS_2$ and 5.85 g of dicyclohexylcarbodiimide (DCC) in 30 ml methanol at room temperature. The reaction mixture was stirred for four hours, and then the resulting white precipitate was separated from the solution by filtration. Finally, it was washed with water and dried under vacuum. 8.93 g final product was isolated (yield: 89%).

Preparation of Gold Powder

Gold powder was prepared by adapting the reported method from Jeffrey et al.[51]. 1.000 g pure (99.9% purity) metallic gold was dissolved in 4 mL aqua regia (3 mL 37% HCl/1 mL 69% $HNO_3$) and then diluted 5 times by adding distilled water. Sodium metabisulfite was gradually added to the solution while it was being stirred gently. Addition of $Na_2S_2O_5$ was continued until all of the gold was precipitated out from the solution (the color changed from a yellow to a colorless solution). The resulting precipitate was isolated, washed with 1M HCl and then with distilled water and finally dried in an oven. 0.975 g light brown gold powder was obtained (yield: 97.5%).

(a) Simultaneous Leaching and Solvent Extraction

Effect of HCl Concentration 5.0 mg gold powder (0.025 mmol) was added to a vial containing 5 ml HCl solution with different concentrations (0.1, 0.5, 1, 1.5 and 2M) and 0.22 M $HNO_3$. Then, 26.8 mg (0.075 mmol) ligand I (a)(i) was dissolved in 5 ml dichloromethane and added to the previous solution. The reaction mixture was stirred vigorously for different periods of time. When the reaction was completed, the two phases were separated and the organic phase was stripped with 5 ml 1M $H_2SO_4$ 1 M containing 0.7 M thiourea for 15 min.

The gold content of the strip solutions was analyzed by AAS. Initial investigations (Table 1) showed that there was a significant difference between conventional leaching by $HCl/HNO_3$ versus simultaneous leaching and extraction employing dithiobiuret ligands (entry 3 vs 4). While not wishing to be limited by theory, the initial tiny amount of leached gold is extracted into the organic phase by the sulfur-based ligands, pushing forward the gold leaching equilibrium (Scheme 1) which leads to increased leaching kinetics.

Scheme 1

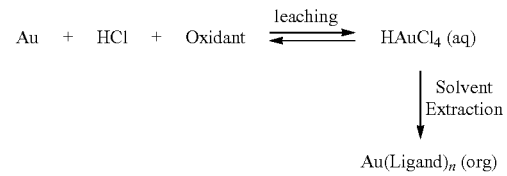

The results showed no significant gold recovery at low HCl concentration (entry 1, 2). However, by increasing HCl concentration gold could be completely recovered at 1M HCl or higher. As can be seen in table 1, more than 99% recovery was achieved in 4 hours when HCl concentration was 1M (entry 4), and at higher molarity the recovery time was shorter (entry 5, 6). Therefore, 1 M (mol/L) HCl was chosen as an acid concentration for other experiments.

Figure 2:
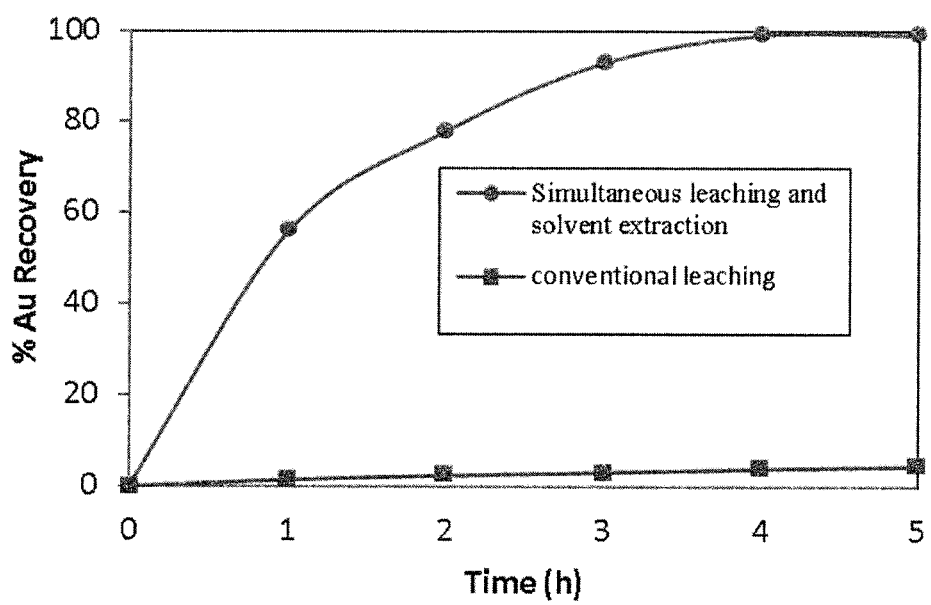
FIG. 2 is a plot showing Au Recovery (%) as a function of time (hours) for simultaneous leaching and extraction according to an embodiment of a method of the present application in comparison to conventional leaching.

Effect of Stirring Time 5.0 mg gold powder (0.025 mmol) was added to a vial containing 5 ml 1M HCl and 0.22 M $HNO_3$. Then, 26.8 mg (0.075 mmol) ligand $L_1$ was dissolved in 5 ml dichloromethane and added to the previous solution. The reaction mixture was stirred vigorously for different periods of time. When the reaction was completed, the two phases were separated and the organic phase was stripped with 5 ml $H_2SO_4$ (1M) containing 0.7 M thiourea for 15 min. The gold content of the strip solutions was analyzed by AAS. The results obtained (FIG. 2) showed that the gold recovery percentage increased quickly with the simultaneous leaching and extraction system until it reached 99% after 4 hours and remained constant. This is significantly quicker than conventional leaching systems with the same amount of HCl and $HNO_3$. A useful leaching time for Au recovery using the present system was found to be 4 h in 1M HCl solution.

A comparison of the conventional leaching system to that of the present study shows that the dithiobiuret ligands can efficiently improve the rate of gold leaching with the least amount of acid and oxidizing reagent. In addition to the leaching step, the new technique recovers gold from aqueous solution at the same time; hence the overall time of gold recovery can be much shorter in comparison to cyanide leaching followed by activated carbon adsorption.

Effect of Ligand Concentration 5.0 mg gold powder (0.025 mmol) was added to a vial containing 5 ml 1M HCl and 0.22M $HNO_3$. Then, different amounts of ligand $L_1$ (Table 2) were dissolved in 5 ml dichloromethane and added to the previous solution. The reaction mixture was stirred vigorously for 4h. When the reaction was completed, the two phases were separated and the organic phase was stripped with 5 ml $H_2SO_4$ (1M) containing 0.7 M thiourea for 15 min. The gold content of the strip solutions was analyzed by AAS.

Table 2 shows the gold recovery percentage with different ligand to Au ratios. With a 1:1 molar ratio, only 42% of gold was recovered with optimized HCl and oxidant concentrations. Gold recovery increased with increasing ligand concentration in organic solvent and substantially completed at a 3:1 molar ratio (L: Au).

Efficiency of Different Ligand Derivatives

Different derivatives of dithiobiuret ligand (I (a)(i) to I (a)(iv)) were synthesized and their capabilities were investigated for simultaneous leaching and extraction of gold in HCl media (Scheme 2). Compared to a monodentate thiourea derivative ($L_1$) and conventional gold extractant, dibutylcarbitol (DBC), all of the dithiobiuret derivatives showed a higher percent gold recovery.

Scheme 2

I(a)(i)
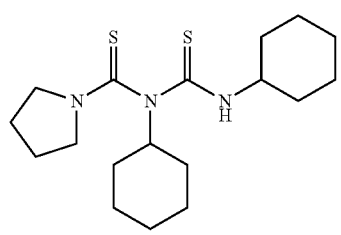

I(a)(ii)
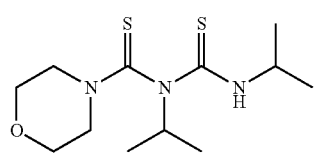

I(a)(iii)
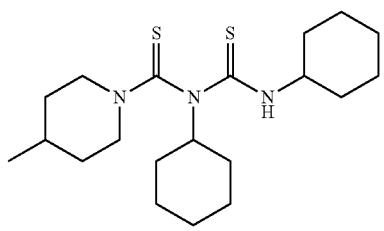

I(a)(iv)
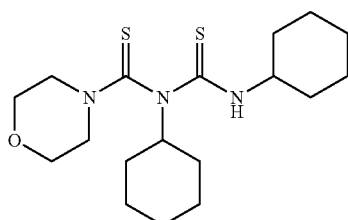

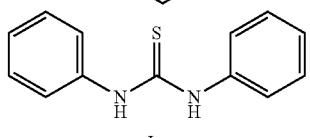
$L_1$

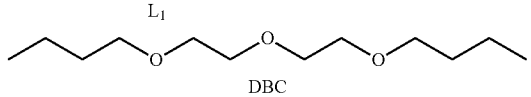
DBC

I(b)(i)
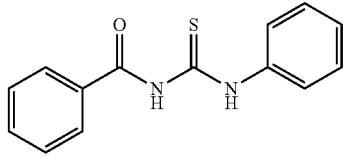

Among the different dithiobiuret derivatives (I (a)(i) to I (a)(iv)), I (a)(i) showed the highest Au recovery %. DBC is the most common gold extractant which is used for selective extraction of gold from acidic solution. Although it is an effective gold extractant in conventional solvent extraction techniques, it showed very low gold recovery under the present simultaneous leaching and extraction conditions even at extremely high concentrations of extractant (entry 6, Table 3).

The ligand I (b)(i) was also investigated. 5.0 mg gold powder (0.025 mmol) was added to a vial containing 5 ml HCl (1M) and $HNO_3$ (0.22 M). Then, 20.3 mg (0.075 mmol) of the synthesized ligand I (b)(i) was dissolved in 5 ml dichloromethane and added to the previous solution. The reaction mixture was stirred vigorously for 6 hours. When the reaction was completed, the two phases were separated and the organic phase was stripped with 5 ml $H_2SO_4$ (1M) containing 0.7 M thiourea for 15 minutes. The gold content of the strip solutions was analyzed by AAS. The results showed that 99.0% of gold was recovered.

Selectivity

To investigate the selectivity of the present technique, a mixture of different metals in chloride form was treated by the system. A mixture of Fe (1000 ppm), Cu (2000 ppm), Zn (500 ppm), Ag (200 ppm) and 0.5 mg gold powder was added to a vial containing 1M 5 ml HCl and 0.2M $HNO_3$. Then, 26.8 mg of ligand $L_1$ was dissolved in 5 ml dichloromethane and added to the previous solution. The reaction mixture was stirred vigorously for different periods of time. When the reaction was completed, the two phases were separated and the organic phase was stripped with 5 ml 1M $H_2SO_4$ containing 0.7 M thiourea for 15 min. The metal content of the post extraction and strip solutions were analyzed by AAS.

The obtained results, shown in Table 4, demonstrate that the simultaneous leaching and extraction technique employing dithibiuret ligands is highly selective for gold, so that only trace amounts of base metals is extracted even at the presence of high amount of free ligand. In contrast to the cyanidation process, the present technique can, for example eliminate the entire activated carbon step for separation of gold from other impurities.

Effect of Organic Solvent

Simultaneous leaching and extraction tests were performed in the water-immiscible organic solvents shown in Table 5. The results show many organic solvents are suitable for extraction and recovery of gold. Among the investigated solvents, the highest percentages of Au recovery were obtained when dichloromethane (DCM), chlorobenzene, or chloroform were used as solvent.

(b) Gold Ore Treatment

Crushed and ground gold ore with an average gold concentration of 7 ppm and an average particle size of 74 microns was obtained from Claude Resources from their Seabee gold mine operation located in the La Ronge Mining District at the north end of Laonil Lake approximately 125 kilometres northeast of the town of La Ronge, Saskatchewan.

Figure 3:
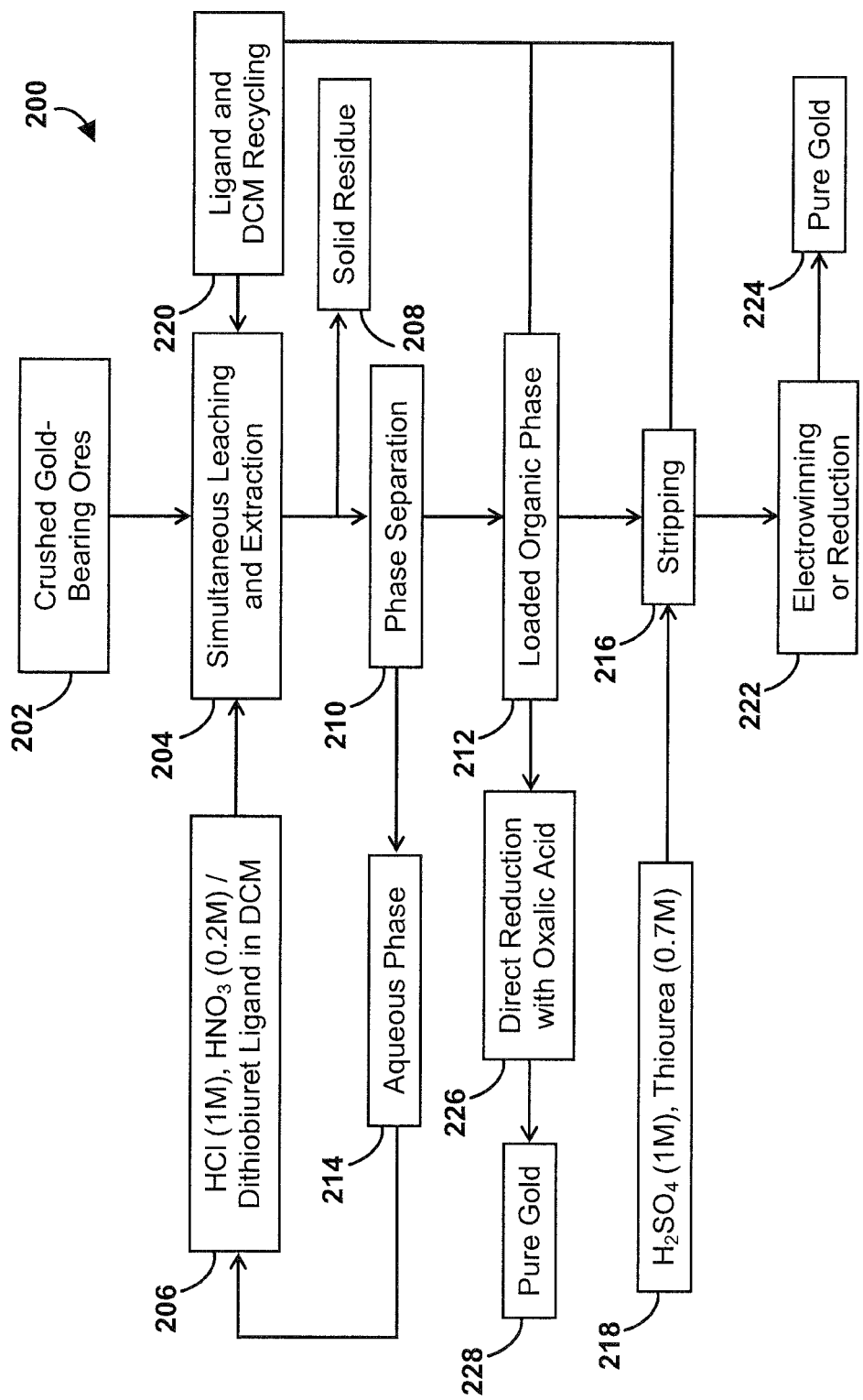
FIG. 3 shows a schematic representation of a method of leaching and extracting gold from a gold-containing substance.

General Experimental for Simultaneous Leaching and Solvent Extraction:

A method flow chart for the simultaneous leaching and solvent extraction technique 200 of the present example is shown in FIG. 3. In the method 200, crushed and ground gold ore 202 with an average particle size of 74 microns was subjected to a simultaneous leaching and extracting step 204 wherein the ore 202 was added to a 1M HCl solution in the presence of $HNO_3$ and a solution of ligand I (a)(i) in dichloromethane was then added to the aqueous solution 206. The resulting biphasic reaction mixture was stirred vigorously for 5h. The mixture was then filtered to remove solid residue 208 and the phases separated 210 into an organic phase 212 and an aqueous phase 214. The aqueous phase 214 can be recycled for use in the simultaneous leaching and extracting step 204. The organic phase 212 was then stripped 216 with 1M $H_2SO_4$ containing 0.7 M thiourea 218 for 15 min, and the gold content of the stripped solutions was analyzed by AAS showing gold recovery efficiencies consistently in the 95-97% range. Subsequent to the stripping step 216, the ligand and DCM can be recycled 220 for use in the simultaneous leaching and extraction step 204. An electrowinning or reduction step 2222 can be carried out to isolate pure gold 224. Alternatively, instead of stripping step 216, the organic phase 212 can be reduced with an agent such as oxalic acid or $NaBH_4$ 226 to provide pure gold 228. If the organic phase is sensitive to a reducing agent, the use of thiourea stripping 216 of gold from the dithiobiuret gold complex may be used. However, the direct reduction 226 of the loaded organic phase may be more economical. For example, in methods 200 comprising stripping 216 the organic phase, a subsequent electrowinning or reduction step 222 is used to obtain the metallic gold 224 whereas in methods 200 comprising a direct reduction step 226, the metallic gold 228 can be obtained with one less step. In the present experiments, because low concentrations of gold in the samples were used, and the efficiency of the systems was measured, the final gold solutions were analyzed. Instead of weighing the precipitated gold, therefore the organic phase was typically stripped and its gold content measured by AAS.

Exemplary Experimental for Simultaneous Leaching and Solvent Extraction:

5.0 g of crushed and ground gold ore with an average particle size of 74 microns was added to a vial containing 5 ml of 1M HCl and 0.55 M $HNO_3$. 27.8 mg of ligand I (a)(i) dissolved in 5 ml of dichloromethane was then added to the aqueous solution. The reaction mixture was stirred vigorously for 5h. The biphasic reaction mixture was then filtered and the organic phase was isolated. The organic phase was then stripped with 5 ml $H_2SO_4$ (1M) containing 0.7 M thiourea for 15 min, and the gold content of the stripped solutions was analyzed by AAS. The final solution contained 6.7 ppm gold (96% gold recovery).

(c) Comparative Example: Gold Ore Treatment with Cyanide Solution:

5.00 g gold ore was added to a vial containing 10 ml basic solution (pH=10.5, pH was adjusted by dissolving the appropriate amount of KOH in distilled water). 0.20 g KCN was added to the solution and the reaction mixture (open to air) was stirred vigorously for 24 hours. The reaction mixture was weighed before starting and after completion of the reaction to estimate the amount of water evaporated during the leaching process. Then the appropriate amount of water was added to the reaction mixture to keep the slurry's density constant. The gold content of the resultant solution was measured by atomic absorption spectroscopy.

This experiment was conducted to determine the amount of gold in the ore sample and to compare the efficiency of the solvent extraction technique of the present studies with the cyanide leaching process. The cyanidation experiment was repeated 20 times on gold ore from the Claude Resources mine, and the results showed the average gold content was between 9.5 and 10 ppm.

(d) Discussion: Solvent Extraction Technique as a Leaching Technique

Appropriate sulfur-containing compounds are useful candidates for gold recovery from ores, because in conformity with Pearson's concept of "hard acid/soft acid and hard base/soft base", precious metals such as gold are typically classified as soft acids while sulfur containing compounds are classified as soft bases. Therefore, appropriate sulfur containing ligands, such as chelating ligands, can be used as highly selective extractants for extraction and recovery of gold[49].

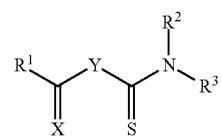

I

Compounds of Formula I wherein, for example, $R^1$ is $-NR^4R^5$; X is S; and Y and $R^2$-$R^5$ are as defined herein are useful for selective extraction of precious metals such as gold from aqueous solutions. Compounds of Formula I wherein, for example, $R^1$ is aryl; X is O; and $R^1$-$R^3$ are as defined herein are also useful for selective extraction of precious metals such as gold from aqueous solution. For example, when X is S, the ligand has two strong donor sites (thiocarbonyl groups) to bind with precious metals which make it a strong bidentate ligand which can form highly stable six-membered ring complexes with precious metals like gold (e.g. compounds of Formula II (a) wherein M comprises a precious metal e.g. Au; and Y and $R^2$-$R^5$ are as defined herein).

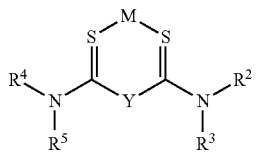

II(a)

In addition, based on the resonance contributors depicted in Scheme 3, the nitrogen atoms will increase the Lewis basicity at the sulfur atoms, making the sulfur electrons more available to donate to the metal center (further resonance contributors exist when Y=N or S rather than C).

In the present studies, both leaching and extraction steps are done simultaneously under mild conditions which increased the overall efficiencies of the process. As shown in Scheme 1, above, this is accomplished by forcing the reaction equilibrium to the right by withdrawing the dissolved gold from aqueous solution containing small amounts of acid and oxidant into the organic phase containing the ligand. In such a process, highly efficient ligands are used which are able to extract even very small amounts of dissolved gold.

In known processes, solvent extraction is usually applied after the leaching step. As far as the inventors are aware, Scheme 3

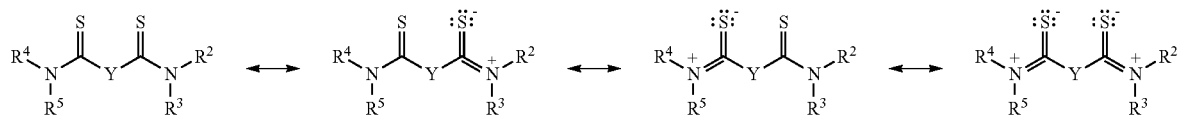

Ligands wherein X=O and $R^1$=aryl behave similarly but were found to take longer to dissolve the gold; e.g. six hours to completely dissolve gold compared to four hours for the dithiobiuret ligands (X=S) studied.

In a typical known solvent extraction process, the desired metal would first be dissolved into water using large amounts of acid in the presence of an oxidant such as hydrogen peroxide or $HNO_3$. In a second step, the metal would then be extracted into an organic phase. Subsequent processing would then usually be required to remove other metal impurities that were also extracted in the process. The solvents would then be removed and the desired metal would be reduced back to its base metal form.

Hydrochloric acid in combination with strong oxidants like $HNO_3$, $H_2O_2$ and $Cl_2$ is a well-known leaching media for gold and other transition metals, but high efficiency is only achieved when high concentrations of acid and oxidant are used. By decreasing the hydrochloric acid concentration in known processes, the leaching kinetic decreases dramatically. However, by keeping the oxidant and HCl concentrations high, their consumption will not be economical and produces a highly corrosive media. In addition, in the case of gold ores, the temperature also is typically increased to obtain an effective leaching.

The derivative of dithiobiuret shown in Scheme 4 has been disclosed as a ligand for selective extraction of gold from hydrochloric acid media[49].

Scheme 4 performing both steps at the same time to improve the leaching step (as well as overall extraction rates) has never been reported before.

Example 2

Simultaneous Leaching and Solvent Extraction of Palladium 5.0 mg palladium powder (0.047 mmol) was added to a vial containing 5 ml water containing HCl (1M) and $HNO_3$ (0.22 M). Then, 64.95 mg (0.184 mmol) of ligand I (a)(i) was dissolved in 5 ml dichloromethane and added to the previous solution. After 2 hours, the palladium was completely dissolved. The two phases were separated and the organic phase (dark brown) was stripped with 5 ml $H_2SO_4$ (1M) containing 0.7 M thiourea for 15 minutes. Then, the yellow precipitate was filtered off and heated up in a furnace to 700° C. to produce a fine black palladium powder (99.3% of palladium was recovered).

Example 3

Gold Leaching in Organic Solvents

A mixture of hydrochloric acid and hydrogen peroxide was chosen as leaching reagent in different water-miscible or partially water-miscible organic solvents. 5.0 mg gold powder was added to 5 ml organic solvent containing 500 mg concentrated HCl (37% w/w) and 60 mg $H_2O_2$ (30% w/w) and stirred for different time periods. After the reaction was complete, the dissolved gold was precipitated and the resultant precipitate was dissolved in aqua regia and purified by the solvent extraction system.[49] The gold content of the final solution was analyzed by AAS. In the case of incomplete gold dissolution, the loaded organic phase was separated from the leftover gold by filtration.

Among the different solvents shown in Table 6, both ethyl acetate and acetonitrile showed the highest % Au leaching in a very short time (14 min), in spite of low concentrations of HCl (1M) and oxidant (0.1 M). These results showed a very short leaching time by ethyl acetate or acetonitrile solutions containing small amounts of both HCl and $H_2O_2$.

Table 7 provides an overview of the results of gold leaching in ethyl acetate, acetic acid and acetonitrile containing different concentrations of HCl and oxidant ($H_2O_2$ or $Ca(ClO)_2$)) in comparison to a system using aqua regia. In each of the trials, 5.0 mg gold powder was dissolved in 5 mL of the organic solvent which contained different amounts of HCl and oxidant as specified in Table 7. Much higher concentrations of oxidant ($HNO_3$) and HCl are used for the aqua regia system than for the systems using the organic solvents.

The leaching rates observed in these experiments are fast enough that particle size is not so much of an issue.

Figure 4:
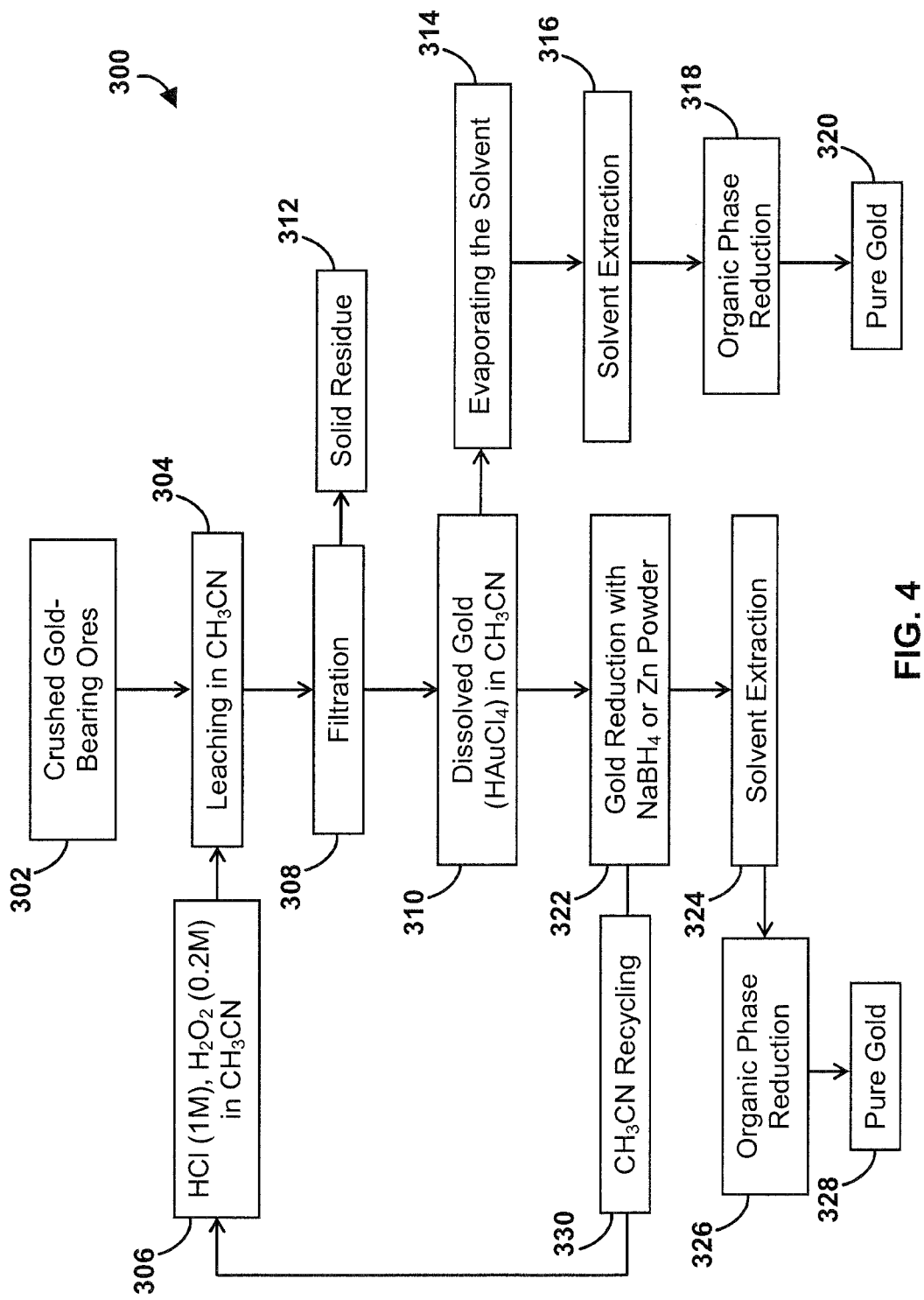
FIG. 4 shows a schematic representation of a method of leaching gold from a gold-containing substance according to an embodiment of a method of the present application.

General Experimental Details for Gold ore Leaching in Ethyl Acetate, Acetic Acid, or Acetonitrile A method flow chart for a method 300 comprising leaching in a water-miscible or partially water-miscible organic solvent such as ethyl acetate, acetic acid or acetonitrile is shown in FIG. 4. This technology is useful for high efficiency gold leaching using, for example, low concentrations of HCl and $H_2O_2$ in ethyl acetate, acetic acid or acetonitrile instead of water. In the method 300, crushed and ground gold ore 302 was subjected to leaching step 304 by being added to a water-miscible or partially water-miscible organic solvent such as ethyl acetate, acetic acid or acetonitrile with a 1M concentration of HCl and 0.1 M $H_2O_2$ 306. The resulting mixture was stirred for 4h. The ethyl acetate or acetonitrile was separated from the solid residue 312 to obtain a solution of dissolved gold ($HAuCl_4$) in ethyl acetate, acetic acid or $CH_3CN$ 310 which was then evaporated 314 under vacuum. The resulting precipitate was then dissolved in 0.1 M HCl and the gold was extracted by a solvent extraction process 316 employing I (a)(i) in DCM and finally stripped (not shown) with $H_2SO_4$ (1 M) containing 0.7 M thiourea.[49] The resulting gold contents were determined by AAS demonstrating, for example, a minimum of 99% gold recovery efficiencies. After being stripped, the organic phase can be reduced 318 to obtain pure gold 320. In an alternative pathway, the solution of dissolved gold ($HAuCl_4$) in ethyl acetate, acetic acid or $CH_3CN$ 310 is reduced with an agent such as $NaBH_4$, ferrocene, Fe powder or Zn powder 322. Using a process comprising such a reduction step 322 instead of the above-described process comprising evaporation step 314 may provide certain advantages, for example, because evaporating the solvent is an additional expense requiring, for example energy and elevated temperatures to evaporate the solvent. By reducing the gold with one of the aforementioned reducing agents, the evaporating step 314 can be eliminated and the solvent can be directly recycled. The gold thereby obtained after the reduction step 322 can then be subjected to a solvent extraction process 324 employing, for example, I (a)(i) in DCM and stripped (not shown) with 1M $H_2SO_4$ containing 0.7 M thiourea. After being stripped, the organic phase is reduced 326 to obtain pure gold 328. The ethyl acetate, acetic acid or $CH_3CN$ which was removed after the reduction step 322 can be recycled 330 for use in the leaching step 304. The solvent extraction steps (316, 324) in the method 300 are useful, for example, to remove impurities such as copper which can be reduced along with gold. Such solvent extraction steps (316, 324) may comprise a conventional leaching and solvent extraction step (i.e. leaching in aqua regia) or alternatively, may comprise, for example, a method of leaching and extracting gold from a gold-containing substance in one step as described herein.

Exemplary Experimental Details for Gold ore Leaching in Ethyl Acetate, Acetic Acid or Acetonitrile:

5.0 g of crushed and ground gold ore with an average particle size of 74 microns was added to 5 ml ethyl acetate, acetic acid or acetonitrile containing 350 mg concentrated HCl and 200 mg $H_2O_2$ 30% w/w. The resulting mixture was stirred for 4h. The ethyl acetate, acetic acid or acetonitrile was separated from the solid residue and evaporated under vacuum. The resulting precipitate was then dissolved in 2 ml 0.1M HCl and the gold was extracted by a solvent extraction process employing 27.2 mg I (a)(i) in 2 ml DCM and finally stripped with 2 ml 1M $H_2SO_4$ containing 0.7 M thiourea. The resulting gold contents were determined by AAS demonstrating 96-97% gold recovery efficiencies.

Example 4

Reduction of Leached Gold in Different Organic Solvents

For each test, 5 ml of organic solvent (which contained 0.5 grams of 37% HCl; i.e. the molarity of the HCl in the organic solvent was 1M) containing different amounts of gold as shown in Table 8 was treated with the indicated reducing reagent for 10 minutes. In the case of Fe powder, the stirring time was 2 hours. The concentration of gold solutions was measured by AAS.

Example 5

Dissolution of Palladium in Organic Solvents

A mixture of hydrochloric acid and hydrogen peroxide was chosen as leaching reagent in different water-miscible or partially water-miscible organic solvents (ethyl acetate, acetic acid, or acetonitrile). 5.0 mg palladium powder (200 mesh) was added to a stirred mixture of 5 ml organic solvent (ethyl acetate, acetic acid, or acetonitrile) containing 500 mg concentrated HCl (37% w/w) and 60 mg $H_2O_2$ (30% w/w) at room temperature. After 15 minutes, the palladium powder was completely dissolved and a clear red solution was obtained.

Example 6

Dissolution of Platinum in Organic Solvents

To a stirred organic solvent (ethyl acetate, acetic acid, or acetonitrile) containing 500 mg concentrated HCl (37% w/w) and 60 mg $H_2O_2$ (30% w/w), 5 mg platinum powder (200 mesh) was added at room temperature. After 90 minutes, the platinum powder was completely dissolved and a pale yellow colored solution was obtained.

Example 7

Figure 5:
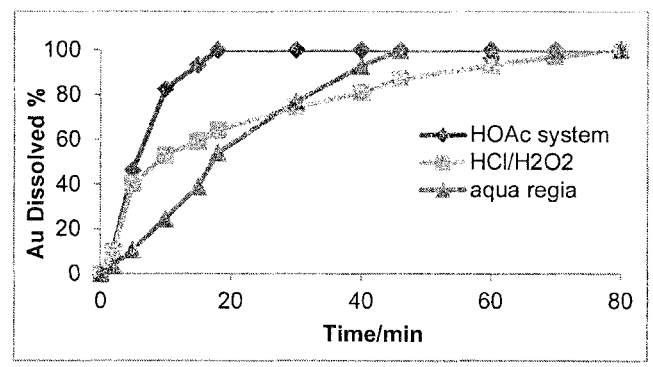
FIG. 5 is a plot showing comparison studies of gold dissolution rate between aqua regia, concentrated HCl/$H_2O_2$, and acetic acid systems.

Effect of Halide Salt Addition to Acid Mixtures (a) Measuring the Rate of Gold Dissolution 120 mg (0.610 mmol) of gold wire (99.9%) with a diameter of 0.25 mm was placed in 20 ml acetic acid containing the desired amounts of acid, oxidant and optionally $CaCl_2$ and stirred at 800 rpm (stir plate setting) for varying time periods (10-60 min) at varying temperatures. The remaining gold wire was then removed from the reaction mixture, washed with acetone and air-dried. The remaining wire was then weighed to calculate the amount of dissolved gold. Based on wire diameter, mass change and dissolution time a dissolution rate was then determined. Table 9 shows the rate of gold dissolution under varying conditions at room temperature. FIG. 5 shows a comparison between the gold dissolution rate of aqua regia, concentrated HCl/$H_2O_2$ and acetic acid systems. Reagent concentrations in acetic acid were HCl (1.5 M), $H_2O_2$ (0.6 M), and $CaCl_2$ (0.6 M). The HCl/$H_2O_2$ mixture was freshly prepared by mixing 4 parts of conc. HCl with one part of $H_2O_2$ 30%.

(b) Gold Ore Treatment 5.00 g of gold ore was added to the desired amounts of acetic acid (5.0 ml or 10.0 ml) containing the desired amounts of HCl, $H_2O_2$ and $CaCl_2$. The resulting mixture was stirred at 800 rpm for varying time periods. The acetic acid was separated from the solid residue by centrifuge (1 min) and evaporated under vacuum. The resulting residue was then dissolved in 2.0 ml of 1M HCl and its gold content was determined by ICP-OES (Table 10).

(c) Selective Gold Stripping from Printed Circuit Boards 20 g printed circuit boards (PCBs) without shredding were added to a 100 ml acetic acid solution including 0.5 M HCl, 0.2 M $CaCl_2$ and 0.2 M $H_2O_2$, and stirred for 2 min. The treated pieces were separated and washed with water, then treated with hot aqua regia to see if any gold was left. ICP revealed that more than 99% of gold was leached while less than 5% of Ni and 1% of copper were dissolved. The same solution was reused 75 times for leaching gold from new PCBs before any loss in activity was observed (i.e. 1.5 kg PCBs were treated with 100 ml HOAc solution in total).

Gold leaching from PCBs using the HOAc system (including 0.5 M HCl, 0.2 M $H_2O_2$ and 0.2 M $CaCl_2$) at r.t in less than 20 seconds resulted in selective gold dissolution (i.e. the underlying nickel was still present).

(d) Results and Discussion

Disclosed herein is a new gold leaching system with the highest gold dissolution rate published to date. This system employs acetic acid as a solvent and contains very low concentrations of an additional acid and an oxidant. Along with an unmatched gold dissolution rate, this new leaching system is also highly selective for gold over base metals such that gold can be dissolved even faster than iron, nickel, cobalt and copper. The efficiency of this new leaching system was examined on gold ore, jewelry scrap and electronic waste (scraps), resulting in >99% of gold leaching at room temperature in only 25 minutes, 10 minutes and 10-20 seconds respectively.

A gold dissolution rate of 6020 $gm^{-2}h^{-1}$ for gold (three times faster than that of aqua regia) at room temperature has been obtained by using acetic acid as solvent under mild conditions (Tables 9, 11). This result represents the fastest recorded rate known for gold dissolution in either organic or aqueous systems (considerably faster than any other known system). Heating the system to 60° C. increases the gold dissolution rate even further to 9000 $gm^{-2}h^{-1}$ (Table 11).

As also can be seen from entries 13 and 14 in Table 11, conducting the dissolution using acetic acid as the solvent resulted in a dramatically higher gold dissolution rate (6020 $gm^{-2}h^{-1}$) in comparison to the gold dissolution rate (5.1 $gm^{-2}h^{-1}$) obtained for a comparative system which used water as the solvent.

Figure 6:
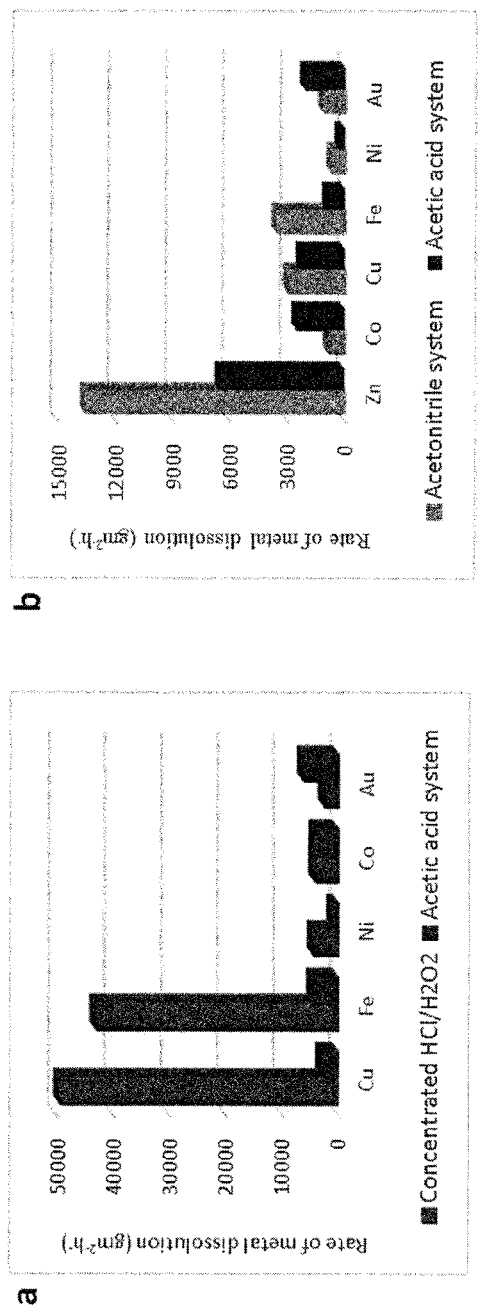
FIG. 6 shows competitive studies of dissolution rates of gold vs. base metals in: (a) Concentrated HCl/$H_2O_2$ mixture (four parts HCl (37%) and one part $H_2O_2$ (30%)) vs. acetic acid (including 1.5 M HCl, 0.6 M $H_2O_2$, and 0.6 M $CaCl_2$) (b) Acetonitrile solution (including 1 M HCl and 0.2 M $H_2O_2$) vs. acetic acid (including 0.5 M HCl, 0.2 M $H_2O_2$, and 0.2 M $CaCl_2$).

In addition to its substantially faster dissolution kinetics, this new leaching method has a much higher affinity for gold over base metals in comparison to concentrated HCl/$H_2O_2$ and aqua regia systems, resulting in gold being dissolved faster than most base metals (FIG. 6).

This selectivity results in reduced reagent consumption and contributes to making this extraction technique more economical than both aqua regia and concentrated HCl/$H_2O_2$.

This acetic acid process is not only the fastest gold dissolution system known, it is also, for example, easy to perform, energy efficient and safer than aqua regia or cyanide systems. By being recyclable, the acetic acid system generates the least amount of liquid waste compared to other systems and also eliminates the requirement for massive water consumption compared to the cyanidation process which can lead to widespread applications of this new technology in remote gold mines which do not have access to water sources. Table 11 compares the efficiency of this extraction method based on the rate of gold dissolution with reported leaching systems. The acetic acid process is substantially more efficient than the reported leaching methods while maintaining mild operating conditions. The fast kinetics of the new leaching system along with low reagent consumptions, simple chemistry, ambient temperature processing and use of commercially available and more environmentally benign reagents make this new leaching system of use for large-scale operations of gold extraction from all gold-bearing materials.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Full Citations for Documents Referred to in the Application

[1] J. Mardsen, I. House, *The Chemistry of Gold Extraction.* 1992, West Sussex, England.

[2] E. B. Amey, "Gold" USGS Mineral Yearbook 2004 (Washington, D.C., USGS, 2004), pp. 34.1-34.9.

[3] Anonymous, "Gold" Mining Journal, (June 11, 2004), pp. 19-24.

[4] A. C. Grosse, G. W. Dicinoski, M. J. Shaw, P. R. Haddad, *Hydrometallurgy* 2003, 69, 1-21.

[5] I. Chandra, M. I. Jeffrey, *Hydrometallurgy* 2005, 77, 191-201.

[6] G. A. Munoz, J. D. Miller, *Minerals and Metallurgical Processing,* 2000, 17, 198-204.

[7] Dai, X., Breuer, P. L., Jeffrey, M. I. *Minerals & Metallurgical Processing,* 2010, 27, 190-195.

[8] M. D. Adams, B. Sceresini, Elsevier, 2005, 789-824.

[9] J. Z. Jiang, W. J. Zhou, H. C. Gao, J. G. Wu, G. X. Xu, and J. Chen. *J. Inorg. Chem.* 2001, 17, 343-48.

[10] P. D. Kondos, G. Deschénes, R. M. Morrison, *Hydrometallurgy,* 1995, 39, 235-250.

[11] F. Habashi, *A Textbook of Hydrometallurgy,* Métallurgie Extractive Québec,0 Québec City, Canada, second edition, 1999.

[12] G. Q. Lui, W. T. Yen, *Minerals Engineering,* 1995, 8, 111-123.

[13] G. Deschénes, G. Wallingford, *Minerals Engineering,* 1995, 8, 923-931.

[14] Grosse, A. C.; Dicinoski, G. W.; Shaw, M. J.; Haddad, P. R. *Hydrometallurgy*, 2003, 69, 1-21.

[15] Dai, X., Breuer, P. L., Jeffrey, M. I. *Minerals & Metallurgical Processing*, 2010, 27, 190-195.

[16] Grosse, A. C. Dicinoski, G. W. Shaw, M. J. Haddad, P. R. *Hydrometallurgy*, 2003, 69, 1-21.

[17] J. Z. Jiang, W. J. Zhou, H. C. Gao, J. G. Wu, G. X. Xu, and J. Chen. *J. Inorg. Chem.* 2001, 17, 343-48.

[18] X. M. Zhang, G. Senanayake, M. J. Nicol, *Hydrometallurgy*, 2004, 74, 243.

[19] G. Rabai, I. R. Epstein, *Inorg. Chem.* 1992, 31, 3239.

[20] S. Zhang, M. J. Nicol, *J Appl. Electrochem*, 2003, 33, 767.

[21] Ritchie, I. M., Nicol, M. J., Staunton, W. P., Young, C. (Ed.), *Cyanide*: Social and Economic Aspects. TMS, Warrendale, 2001, pp. 427-440.

[22] Berezowsky, R. M. G. S., Sefton, V. B., 108th *AIME Annual Meeting, New Orleans, La.,* 1979, pp. 1-17.

[23] Aylmore, M. G., Muir, D. M, *Miner. Eng.* 2001, 14, 135-174.

[24] Breuer, P. L., Jeffrey, M. I., *Hydrometallurgy*, 2003, 70, 163-173.

[25] Feng, D., van Deventer, J. S. J., *Hydrometallurgy*, 2006, 82, 126-132.

[26] Kazakov, V. P.; Lapshin, A. I.; Peshchevitskii, B. I. Russ. J. *Inorg. Chem.* 1964, 9, 708.

[27] Plaskin, I. N. and Kozhukhova, M. A, Sbornik Nauchnyhk Trudov, *Institut Tsvetnykh Metallov*, 1960, 33, 107-119.

[28] Preisler, P. W. and Berger, L., *Journal of the American Chemical Society*, 1947, 69, 322-325.

[29] Schulze, R. G., 1984, *Journal of Metals*, 1984, 36, 62-65.

[30] Groenewald, T., *Hydrometallurgy*, 1976, 1, 277-290.

[31] Gönen, N., *Hydrometallurgy*, 2003, 69, 169-176.

[32] Krzewska, S. and Podsiadly, H., *Journal of Inorganic and Nuclear Chemistry*, 1980, 42, 83-86.

[33] Örgill, S., Atalay, Ü. *Hydrometallurgy*, 2002, 67, 71-77.

[34] J. W. Mellor, *A Comprehensive Treatise of Inorganic and Theoretical Chemistry* (London: Longman Green & Co., 1923), p. 499.

[35] F. Habashi, *Principles of Extractive Metallurgy, Vol. $2^{nd}$* ed. (New York: Gordon and Breach, 1980), p. 39.

[36] Finkelstein, N. P., Hoare, R. M., James, G. S., Howat, D. D., *Journal of the South African Institute of Mining and Metallurgy*, 1996, 67, 196-215.

[37] Filmer, A. O., Lawrence, P. R., Hoffman, W., 1984. *A comparison of cyanide, thiourea, and chlorine as lixiviants for gold*. Gold—Mining, Metallurgy, and Geology. Australasian Institute of Mining and Metallurgy, Melbourne, pp. 279-287.

[38] Ikiz, D., Gulfen, M., Aydin, A. O. *Minerals Engineering*, 2006, 19, 972-974.

[39] Jeffrey, M. I., Breuer, P. L., Choo, W. L. *Metall. Mater. Trans.* 2001, B 32, 979-986.

[40] Nesbitt, C. C., Milosavljevic, E. B., Hendrix, J. L.,*Chem. Res.* 1990, 29, 1696-1700.

[41] Ghobeiti Hasab, M., Rashchi, F., Raygan, Sh. *Miner. Eng.* 2013, 50-51, 140-142.

[42] Ghobeiti Hasab, M., Raygan, Sh., Rashchi, F., *Hydrometallurgy*, 2013, 138, 59-64.

[43] Cheng, Y. Shen, S. Zhang, J. Chen, S. Xiong, L. Liu J. Ind. Eng. Chem. Res. 2013, 52, 16622-16629.

[44] Parker, A. J. Muir, D. J. Smart, Y. C. Avraamides, *J. Hydrometallurgy*, 1981, 7, 213-233.

[45] Yoshimura, A. Takai, M. Matsuno, Y. *Hydrometallurgy*, 2014, 149, 177-182.

[46] Gill, J. B. Goodall, D.C. Jeffreys, B. *Hydrometallurgy*, 1984, 13, 221-226.

[47] Lin, W. Zhang, R. W. Jang, S. S. Wong, C. P. Hong, *J. Angew. Chem. Int. Ed.* 2010, 49, 7929-7932.

[48] Yukimichi, N. *J. Chem. Soc., Chem. Commun.* 1992, 426-427.

[49] Moradi, L. Salimi, H. Piltan, M. Yavari, I. *United States Patent. Pub. No. US* 2012/0228151 Al. Sep. 13, 2012.

[50] Vest, P. Schuster, M. Konig, K. H. Fresenius *J Anal Chem.* 1991, 341, 556-568.

[51] Jeffrey, M. Breuer, P. L. Chu, C. K. *Int. J. Miner. Process.* 2003, 72, 323-330.

[52] Oraby, E. A. & Eksteen, J. J. The leaching of gold, silver and their alloys in alkaline glycine—peroxide solutions and their adsorption on carbon. *Hydrometallurgy* 152, 199-203 (2015).

[53] Geoffroy, N. & Cardarelli, F. A method for leaching or dissolving gold from ores or precious metal scrap. *JOM.* 57, 47-50 (2005).

[54] Senanayake, G. Gold leaching in non-cyanide lixiviant systems: critical issues on fundamentals and applications. *Miner. Eng.* 17, 785-801 (2004).

[55] Li, J. et al. Thiocyanate hydrometallurgy for the recovery of gold. Part II: the leaching kinetics. *Hydrometallurgy* 113-114, 10-189 (2012).

[56] Li, J. & Miller, J. D. A review of gold leaching in acid thiourea solutions. *Miner. Process. Extr. Metall. Rev.* 27, 177-214 (2006).

[57] Lin, W., Zhang, R. W. Jang, S. S., Wong, C. P. & Hong, J. I. "Organic aqua regia"—powerful liquids for dissolving noble metals. *Angew. Chem. Int. Ed.* 49, 7929-7932 (2010).

[58] Nam, K. S. et al. Use of chloride—hypochlorite leachants to recover gold from tailing. *Int. J. Miner. Process.* 86, 131-140 (2008).

[59] Nakao, Y. & Sone, K. Reversible dissolution/deposition of gold in iodine—iodide—acetonitrile systems. *Chem. Commun.* 8, 897-898 (1996).

Yoshimura, A., Takai, M. & Matsuno, Y. Novel process for recycling gold from secondary sources: leaching of gold by dimethyl sulfoxide solutions containing copper bromide and precipitation with water. *Hydrometallurgy* 149, 177-182 (2014).

TABLE 1

Simultaneous leaching and extraction of gold powder in different HCl concentrations.

| Entry | HCl (M) | Time (h) | Au Recovery (%) |
|---|---|---|---|
| 1 | 0.1 | 4 | 5.3 |
| 2 | 0.5 | 4 | 20.7 |
| 3 | 1 | 4 | 4.6* |
| 4 | 1 | 4 | 99.2 |
| 5 | 1.5 | 3 | 99.1 |
| 6 | 2 | 2.5 | 99.3 |

*Conventional leaching by HCl/$HNO_3$.

TABLE 2

Simultaneous leaching and extraction of gold powder with different ligand:Au ratios.

| Entry | Ligand:Au | Au Recovery % |
|---|---|---|
| 1 | 1:1 | 42.7 |
| 2 | 2:1 | 72.4 |
| 3 | 3:1 | 99.5 |
| 4 | 4:1 | 99.4 |

TABLE 3

Simultaneous leaching and extraction of gold powder with different ligands.

| Entry | Ligand | Au Recovery % |
|---|---|---|
| 1 | I(a)(i) | 99.7 |
| 2 | I(a)(ii) | 72.4 |
| 3 | I(a)(iii) | 96.5 |
| 4 | I(a)(iv) | 70.4 |
| 5 | $L_1$ | 3.3 |
| 6 | DBC | 5.1* |

*Pure DBC was used as the organic phase.

TABLE 4

Effect of other impurities on simultaneous leaching and extraction of gold (113 ppm of gold was extracted in the presence of large excesses of Fe, Cu and Zn impurities).

|  | Fe | Cu | Zn | Au |
|---|---|---|---|---|
| Aq phase (ppm) | 991.8 | 2140.3 | 542.8 | 0.3 |
| Stripping solution (ppm) | 0.4 | 0.1 | 0.1 | 112.3 |

TABLE 5

Simultaneous leaching and extraction of gold powder in different water-immiscible organic solvents.

| Entry | Solvent | Au Recovery % |
|---|---|---|
| 1 | DCM | 99.9 |
| 2 | Chloroform | 97.4 |
| 3 | Dichloroethane | 68.4 |
| 4 | Chlorobenzene | 98.8 |
| 5 | Dichlorobenzene | 61.3 |
| 6 | Toluene | 56.1 |

TABLE 6

Gold leaching in different water-miscible organic solvents containing HCl and $H_2O_2$.

| Entry | Solvent | Stirring Time (h) | Au Leaching % |
|---|---|---|---|
| 1 | THF | 0.5 | 24 |
| 2 | THF | 5 | 100 |
| 3 | DMF | 24 | 56 |
| 4 | DMSO | 24 | 31 |
| 5 | Ethyl acetate | 0.25 | 100 |
| 6 | MeCN | 0.25 | 100 |
| 7 | MeOH | 24 | 13 |

TABLE 7

Gold leaching in different solvents containing different HCl and oxidant concentrations.

| Entry | Solvent | Oxidant (M) | HCl (M) | Stirring time (min) | Au Leaching % |
|---|---|---|---|---|---|
| 1 | Ethyl acetate | $H_2O_2$(0.10) | 1 | 14 | 100 |
| 2 | Ethyl acetate | $H_2O_2$(0.20) | 1 | 6 | 100 |
| 3 | Ethyl acetate | $H_2O_2$(0.30) | 1 | 4 | 100 |
| 4 | Ethyl acetate | $H_2O_2$(0.10) | 2 | 4 | 100 |
| 5 | Ethyl acetate | $H_2O_2$(0.10) | 2 | 4 | 100 |
| 6 | MeCN | $H_2O_2$(0.10) | 1 | 14 | 100 |
| 7 | MeCN | $H_2O_2$(0.20) | 1 | 6 | 100 |
| 8 | MeCN | $H_2O_2$(0.30) | 1 | 4 | 100 |
| 9 | MeCN | $H_2O_2$(0.10) | 2 | 4 | 100 |
| 10 | MeCN | $H_2O_2$(0.10) | 2 | 4 | 100 |
| 11 | Ethyl acetate | $Ca(ClO)_2$ (0.03) | 1 | 6 | 100 |
| 12 | Ethyl acetate | $Ca(ClO)_2$ (0.05) | 1 | 4 | 100 |
| 13 | Ethyl acetate | $Ca(ClO)_2$ (0.10) | 1 | 3 | 100 |
| 14 | MeCN | $Ca(ClO)_2$ (0.03) | 1 | 6 | 100 |
| 15 | MeCN | $Ca(ClO)_2$ (0.05) | 1 | 4 | 100 |
| 16 | MeCN | $Ca(ClO)_2$ (0.10) | 1 | 3 | 100 |
| 17 | $CH_3COOH$ | $H_2O_2$(0.10) | 1 | 14 | 100 |
| 18 | $CH_3COOH$ | $H_2O_2$(0.20) | 1 | 6 | 100 |
| 19 | $CH_3COOH$ | $Ca(ClO)_2$ (0.03) | 1 | 6 | 100 |
| 20 | $CH_3COOH$ | $Ca(ClO)_2$ (0.05) | 1 | 4 | 100 |
| 21 | Aqua regia | $HNO_3$ (2.92) | 9.6 | 8 | 100 |

TABLE 8

Reduction of leached gold in different organic solvents.

| Entry | Solvent | Reducing agent (mg) | Au concentration before reduction (ppm) | Au concentration after reduction (ppm) | Reduction % |
|---|---|---|---|---|---|
| 1 | Ethyl acetate | Zn powder (20) | 1000 | 5 | 99.5 |
| 2 | Ethyl acetate | Zn powder (10) | 10 | 0 | 100 |
| 3 | Ethyl acetate | $NaBH_4$ (10) | 1000 | 5 | 99.5 |
| 4 | Ethyl acetate | $NaBH_4$ (5) | 10 | 0 | 100 |
| 5 | Ethyl acetate | Fe powder (20) | 1000 | 8 | 99.2 |
| 6 | Ethyl acetate | Fe powder (10) | 10 | 0 | 100 |
| 7 | MeCN | Zn powder (20) | 1000 | 2 | 99.8 |
| 8 | MeCN | Zn powder (10) | 10 | 0 | 100 |
| 9 | MeCN | $NaBH_4$ (10) | 1000 | 6 | 99.4 |
| 10 | MeCN | $NaBH_4$ (5) | 10 | 0.3 | 97.0 |
| 11 | MeCN | Fe powder (20) | 1000 | 12 | 98.8 |
| 12 | MeCN | Fe powder (10) | 10 | 0.1 | 99.0 |
| 13 | $CH_3COOH$ | Zn powder (20) | 1000 | 1 | 99.9 |
| 14 | $CH_3COOH$ | Zn powder (10) | 10 | 0 | 100 |
| 15 | $CH_3COOH$ | $NaBH_4$ (10) | 1000 | 9 | 99.1 |
| 16 | $CH_3COOH$ | $NaBH_4$ (5) | 10 | 0 | 100 |
| 17 | $CH_3COOH$ | Fe powder (20) | 1000 | 8 | 99.2 |
| 18 | $CH_3COOH$ | Fe powder (10) | 10 | 0.5 | 95.0 |

TABLE 9

Gold dissolution rate in acetic acid under varying conditions.

| Entry | HCl (mol/L) | $H_2O_2$ (mol/L) | $CaCl_2$ (mol/L) | gold dissolution rate (gm$^{-2}$h$^{-1}$) |
|---|---|---|---|---|
| 1 | 0.1 | 0.2 | — | 350 |
| 2 | 0.2 | 0.2 | — | 570 |
| 3 | 0.5 | 0.2 | — | 857 |
| 4 | 1.0 | 0.2 | — | 1280 |
| 5 | 1.5 | 0.2 | — | 1285 |
| 6 | 1.0 | 0.1 | — | 850 |
| 7 | 1.0 | 0.3 | — | 1310 |
| 8 | 0.5 | 0.2 | 0.2 | 2100 |
| 9 | 1.0 | 0.2 | 0.1 | 1580 |
| 10 | 1.0 | 0.2 | 0.2 | 2110 |
| 11 | 1.0 | 0.2 | 0.3 | 2120 |
| 12 | 1.0 | 0.3 | 0.3 | 2940 |
| 13 | 1.0 | 0.4 | 0.4 | 3700 |
| 14 | 1.0 | 0.5 | 0.5 | 3720 |
| 15 | 1.5 | 0.4 | 0.4 | 4500 |
| 16 | 1.5 | 0.6 | 0.6 | 6020 |
| 17 | 1.5 | 0.8 | 0.8 | 6018 |
| 18 | 2.0 | 0.8 | 0.8 | 5810 |
| 19 | 3.0 | 1.2 | 1.2 | 4100 |

TABLE 10

Gold ore leaching results by cyanidation process vs acetic acid system under varying conditions at room temperature.

| Sample # | solvent/solid* (v/v) | Time (h) | HCl (M) | $H_2O_2$ (M) | $CaCl_2$ (M) | KCN (M) | Dissolved gold (ppm)*** |
|---|---|---|---|---|---|---|---|
| 1 | 1 | 10 | 1 | 0.4 | 0.4 | — | 9.8 |
| 2 | 2 | 1 | 1 | 0.4 | 0.4 | — | 10.2 |
| 3 | 2 | 0.4 | 1.5 | 0.6 | 0.6 | — | 10.3 |
| 4 | 2 | 5 | 0.5 | 0.2 | 0.2 | — | 9.8 |
| 5** | 2 | 1.5 | 0.5 | 0.2 | 0.2 | — | 9.9 |
| 6 | 2 | 35 | — | — | — | 0.02 | 9.9 |

*For samples 1-5, the solvent was acetic acid, and for sample 6 it was water with pH = 10.5.
**gold leaching was performed at 60° C.
***Gold concentration in ore was 10.4 ppm.

TABLE 11

Comparison of the rate of gold dissolution in different leaching systems.

| Entry | Lixiviant solution | Solvent (t ° C.) | Rate (gm$^{-2}$h$^{-1}$) | Ref. |
|---|---|---|---|---|
| 1 | glycine, $H_2O_2$ | $H_2O$ (rt)* | 0.2 | 52 |
| 2 | NaCN, Ca(OH)$_2$ | $H_2O$ (30) | 0.7 | 53 |
| 3 | Fe$^{3+}$, SC(NH$_2$)$_2$, $H_2SO_4$ | $H_2O$ (rt) | 7 | 54 |
| 4 | SCN$^-$, Fe$^{3+}$ | $H_2O$ (rt) | 7.3 | 55 |
| 5 | Cu$^{2+}$, S$_2$O$_3^{2-}$, NH$_3$ | $H_2O$ (rt) | 27 | 54 |
| 6 | I$_2$, KI | $H_2O$ (35) | 36.4 | 56 |
| 7 | SOCl$_2$/py mixture (3:1) | SOCl$_2$ (rt) | 59 | 57 |
| 8 | OCl$^-$, NaCl, pH = 6 | $H_2O$ (rt) | 130 | 58 |
| 9 | I$_2$, [NEt$_4$]I | MeCN (80) | 189 | 59 |
| 10 | CuBr, KBr | DMSO (75) | 370 | 60 |
| 11 | aqua regia | conc. HCl/HNO$_3$ (rt) | 1850 | present work |
| 12 | conc. HCl/H$_2$O$_2$ | HCl/H$_2$O$_2$ (4:1) (rt) | 2320 | present work |
| 13 | 0.6M H$_2$O$_2$, 0.6M CaCl$_2$ 1.5M HCl | H$_2$O (rt) | 5.1 | present work |
| 14 | 0.6M H$_2$O$_2$, 0.6M CaCl$_2$ 1.5M HCl | acetic acid (rt) | 6020 | present work |
| 15 | 0.6M H$_2$O$_2$, 0.6M CaCl$_2$ 1.5M HCl | acetic acid (60) | 9000 | present work |

*rt = room temperature

The invention claimed is:

1. A method of leaching gold from a substance comprising gold, the method comprising
    (i) leaching the substance with a first mixture comprising:
        (a) an acid;
        (b) an oxidizing agent; and
        (c) a solvent selected from acetic acid, ethyl acetate, acetonitrile, and tetrahydrofuran to provide a second mixture,
    the leaching being done under conditions to leach the gold from the substance, wherein
    the conditions to leach the gold from the substance comprise stirring the substance and the first mixture for a time of about 0.1 minute to about 2 hours at a temperature of about 20° C. to about 60° C., the acid is a hydrogen halide, chlorous acid, chloric acid, bromous acid, bromic acid, iodous acid, iodic acid, perchloric acid, sulfuric acid, oxalic acid, phosphoric acid, an organic acid or combinations thereof, and
    the oxidizing agent is ozone, nitric acid, hydrogen peroxide, $O_2$, bubbled air, $I_2$, $Br_2$, $Cl_2$, potassium monopersulfate, an ammonium polyatomic salt, calcium hypochlorite, a sodium polyatomic salt, a potassium polyatomic salt, manganese oxide, a tetraalkylammonium salt, peroxomonosulfuric acid, urea, peracetic acid, or combinations thereof; and
    (ii) separating insoluble impurities from the second mixture to provide a solution of dissolved leached gold.

2. The method of claim 1, wherein the method further comprises:
    evaporating the solution to provide the leached gold.

3. The method of claim 2, wherein the method further comprises, after evaporating, contacting the leached gold with a compound of Formula I:

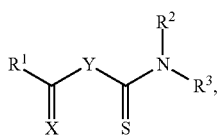

wherein
    $R^1$ is —NR$^4$R$^5$ or aryl;
    $R^2$ and $R^3$ are each independently selected from H, $C_{1-10}$alkyl, $C_{3-10}$cycloalkyl, $C_{1-6}$alkylene$C_{3-10}$cycloalkyl, heterocycloalkyl and aryl; or
    $R^2$ and $R^3$ together with the nitrogen atom to which they are attached, form a heterocycloalkyl or a heteroaryl, or a heterocycloalkyl or a heteroaryl substituted at one or more carbon atoms with $C_{1-4}$alkyl;
    $R^4$ and $R^5$ are each independently selected from H, $C_{1-10}$alkyl, $C_{3-10}$cycloalkyl, $C_{1-6}$alkylene$C_{3-10}$cycloalkyl, heterocycloalkyl and aryl; or
    $R^4$ and $R^5$ together with the nitrogen atom to which they are attached, form a heterocycloalkyl or a heteroaryl, or a heterocycloalkyl or a heteroaryl substituted at one or more carbon atoms with $C_{1-4}$alkyl;
    X is O or S;
    Y is S, NR$^6$ or CR$^6$R$^7$; and
    $R^6$ and $R^7$ are each independently selected from H, $C_{1-10}$alkyl, $C_{3-10}$cycloalkyl, $C_{1-6}$alkylene$C_{3-10}$cycloalkyl, heterocycloalkyl and aryl,
under conditions to form a complex between the compound of Formula I and the leached gold.

4. The method of claim 3, wherein Y is $NR^6$.

5. The method of claim 3, wherein the compound of Formula I is a compound of Formula I (a)(i), I (a)(ii), I (a)(iii) or I (a)(iv):

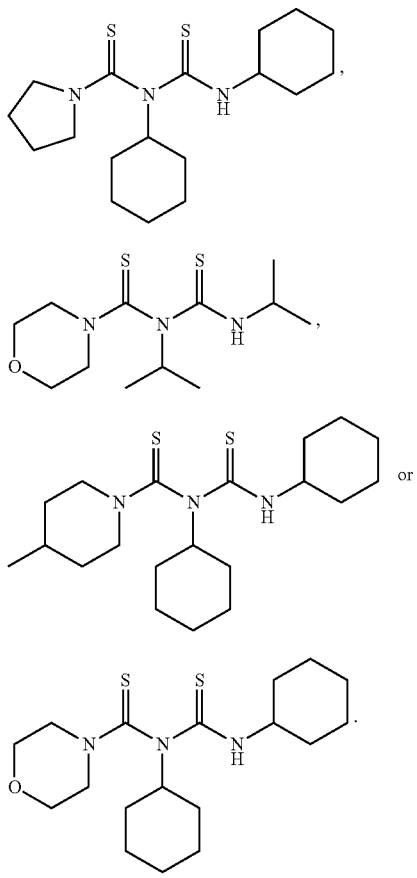

6. The method of claim 3, wherein the conditions to form the complex between the compound of Formula I and the leached gold comprise contacting the solution with the compound of Formula I in a water-immiscible organic solvent for a time of about 2 minutes to about 30 minutes at a temperature of about 10° C. to about 40° C.

7. The method of claim 3, wherein the method further comprises stripping the gold from the complex between the compound of Formula I and the leached gold by a method comprising contacting the water-immiscible organic solvent containing the complex between the compound of Formula I and the leached gold with an aqueous solution comprising an acid and thiourea under conditions to obtain a gold-containing gold strip solution and a gold-reduced organic phase comprising the compound of Formula I.

8. The method of claim 7, wherein the method further comprises separating the gold-containing strip solution from the gold-reduced organic phase comprising the compound of Formula I and recovering gold from the gold-containing strip solution by electrowinning or reduction.

9. The method of claim 1, wherein the method further comprises:
contacting the solution with a reducing agent under conditions to obtain gold; and
separating the gold from the solution.

10. The method of claim 9, wherein the method further comprises, after separating the gold from the solution:
dissolving the gold in aqua regia; and
contacting the dissolved gold with a compound of Formula I:

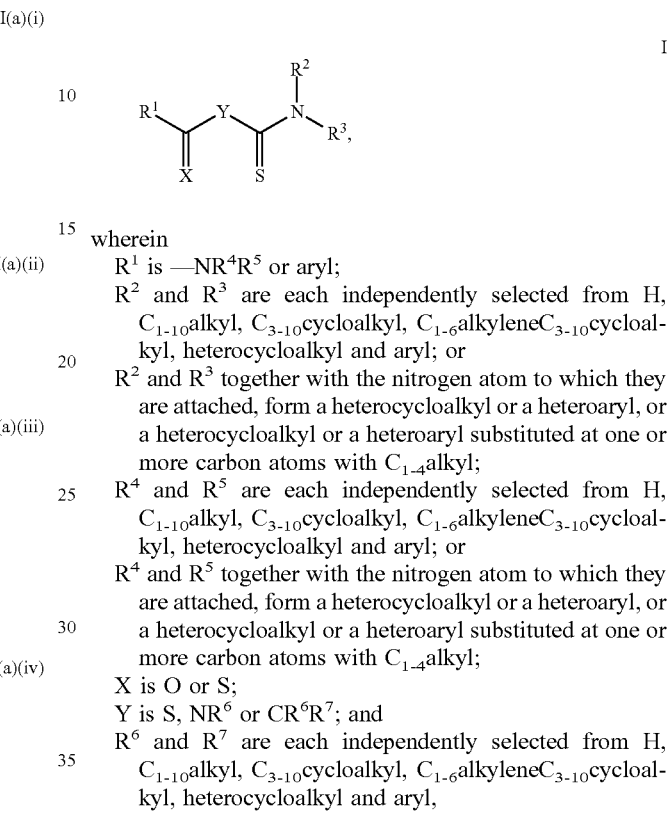

wherein
$R^1$ is $-NR^4R^5$ or aryl;
$R^2$ and $R^3$ are each independently selected from H, $C_{1-10}$alkyl, $C_{3-10}$cycloalkyl, $C_{1-6}$alkylene$C_{3-10}$cycloalkyl, heterocycloalkyl and aryl; or
$R^2$ and $R^3$ together with the nitrogen atom to which they are attached, form a heterocycloalkyl or a heteroaryl, or a heterocycloalkyl or a heteroaryl substituted at one or more carbon atoms with $C_{1-4}$alkyl;
$R^4$ and $R^5$ are each independently selected from H, $C_{1-10}$alkyl, $C_{3-10}$cycloalkyl, $C_{1-6}$alkylene$C_{3-10}$cycloalkyl, heterocycloalkyl and aryl; or
$R^4$ and $R^5$ together with the nitrogen atom to which they are attached, form a heterocycloalkyl or a heteroaryl, or a heterocycloalkyl or a heteroaryl substituted at one or more carbon atoms with $C_{1-4}$alkyl;
X is O or S;
Y is S, $NR^6$ or $CR^6R^7$; and
$R^6$ and $R^7$ are each independently selected from H, $C_{1-10}$alkyl, $C_{3-10}$cycloalkyl, $C_{1-6}$alkylene$C_{3-10}$cycloalkyl, heterocycloalkyl and aryl,
under conditions to form a complex between the compound of Formula I and the dissolved gold.

11. The method of claim 10, wherein the conditions to form the complex between the compound of Formula I and the dissolved gold comprise contacting the dissolved gold with the compound of Formula I in a water-immiscible organic solvent for a time of about 2 minutes to about 30 minutes at a temperature of about 10° C. to about 40° C.

12. The method of claim 11, wherein the method further comprises stripping the gold from the complex between the compound of Formula I and the dissolved gold by a method comprising contacting the water-immiscible organic solvent containing the complex between the compound of Formula I and the dissolved gold with an aqueous solution comprising an acid and thiourea under conditions to obtain a gold-containing strip solution and a gold-reduced organic phase comprising the compound of Formula I.

13. The method of claim 12, wherein the method further comprises separating the gold-containing strip solution from the gold-reduced organic phase comprising the compound of Formula I and recovering gold from the gold-containing strip solution by electrowinning or reduction.

14. The method of claim 1, wherein the first mixture further comprises a metal halide, an ammonium halide, a tetraalkylammonium halide or a combination thereof.

15. The method of claim 1, wherein the substance is a gold-containing ore.

16. The method of claim 1, wherein the method provides a gold dissolution rate of about 500 $gm^{-2}h^{-1}$ to about 9500 $gm^{-2}h^{-1}$.

17. The method of claim 1, wherein the solvent is acetic acid.

18. The method of claim 1, wherein the acid is selected from HCl, $H_2SO_4$, HBr, $H_3PO_4$ and HI.

19. The method of claim 18, wherein the acid is HCl.

20. The method of claim 19, wherein the acid is present in the first mixture at a concentration of from about 0.01M to about 2.5M.

21. The method of claim 1, wherein the oxidizing agent is selected from $H_2O_2$, $Cl_2$, $Br_2$, $I_2$, $Ca(ClO)_2$, $HNO_3$, $MnO_2$, $KMnO_4$ and $K_2Cr_2O_7$.

22. The method of claim 21, wherein the oxidizing agent is $H_2O_2$ or $Ca(ClO)_2$.

23. The method of claim 22, wherein the oxidizing agent is $H_2O_2$ and the $H_2O_2$ is present in the first mixture at a concentration of from about 0.01 M to about 1.0 M.

24. The method of claim 22, wherein the oxidizing agent is $CaClO_2$ and the $CaClO_2$ is present in the first mixture at a concentration of from about 0.005 M to about 0.5 M.

25. The method of claim 1, wherein the method provides a gold dissolution rate of about 1000 $gm^{-2}h^{-1}$ to about 9500 $gm^{-2}h^{-1}$.

26. The method of claim 1, wherein the conditions to leach the gold from the substance comprise stirring the substance and the first mixture at a temperature of about 20° C. to about 40° C.

27. The method of claim 1, wherein step (ii) comprises separating insoluble impurities from the second mixture to provide a solution of dissolved leached gold that remains in solution at room temperature.

28. The method of claim 1, wherein the conditions to leach the gold from the substance comprise stirring the substance and the first mixture at a temperature of about 20° C. to about 25° C.

29. The method of claim 1, wherein the first mixture comprises less than, or equal to, about 17% (w/w) water.

30. The method of claim 1, wherein the solvent is a non-aqueous solvent.

\* \* \* \* \*